US012636502B2

(12) United States Patent　　　(10) Patent No.: US 12,636,502 B2

Loo et al.　　　(45) Date of Patent: May 26, 2026

(54) IMPLANTABLE PULSE GENERATOR WITH SUTURE HOLES, METHODS FOR IMPLANTING THE SAME, AND ENCAPSULATION OF EXTERNAL COMPONENTS IN ACTIVE IMPLANTABLE MEDICAL DEVICES

(71) Applicant: Galvani Bioelectronics Limited, Stevenage (GB)

(72) Inventors: Alexander Loo, South San Francisco, CA (US); Peng Cong, Burlingame, CA (US); David K. Peterson, South San Francisco, CA (US)

(73) Assignee: Galvani Bioelectronics Limited, Stevenage (GB)

( * ) Notice: Subject to any disclaimer, the term of this patent is extended or adjusted under 35 U.S.C. 154(b) by 940 days.

(21) Appl. No.: 17/279,032

(22) PCT Filed: Sep. 23, 2019

(86) PCT No.: PCT/US2019/052403

§ 371 (c)(1),
(2) Date: Mar. 23, 2021

(87) PCT Pub. No.: WO2020/068652

PCT Pub. Date: Apr. 2, 2020

(65) Prior Publication Data

US 2021/0402191 A1　　Dec. 30, 2021

Related U.S. Application Data

(63) Continuation-in-part of application No. 16/140,471, filed on Sep. 24, 2018, now Pat. No. 11,097,115.

(Continued)

(51) Int. Cl.
A61N 1/372　　(2006.01)
A61N 1/36　　(2006.01)
(Continued)

(52) U.S. Cl.
CPC ....... A61N 1/37229 (2013.01); A61N 1/3605 (2013.01); A61N 1/37518 (2017.08); A61N 1/378 (2013.01)

(58) Field of Classification Search
CPC ............ A61N 1/37229; A61N 1/37518; A61N 1/3605; A61N 1/378
(Continued)

(56) References Cited

U.S. PATENT DOCUMENTS 4,441,498 A　　4/1984　Nordling
5,948,001 A　　9/1999　Larsen
(Continued)

FOREIGN PATENT DOCUMENTS

EP　　　　3747504 A1 *　12/2020　......... A61N 1/37229
JP　　　　2012-45103 A　　3/2012
WO　　　2006126201 A2　11/2006

OTHER PUBLICATIONS

Nov. 19, 2019—(WO) ISR & WO—App. No. PCT/US19/52403.
Mar. 23, 2021—(WO) IPRP & WO—App. No. PCT/US19/52403.

*Primary Examiner* — Michael J Lau
(74) *Attorney, Agent, or Firm* — Taft Stettinius & Hollister LLP

(57) ABSTRACT

An implantable pulse generator is provided that includes a power source, a wireless communication component configured to facilitate wireless communication with a non-implanted device and pulse-generating circuitry connected to the power source. The pulse-generating circuitry can be configured to identify, based on wireless communication with the non-implanted device, temporal and amplitude characteristics for electrical pulse stimuli and to trigger electrical output stimuli having the temporal and amplitude characteristics. The implantable pulse generation can further include one or more lead connections—each being shaped to engage a lead and electrically connected to the pulse- (Continued)

generating circuitry to enable the lead to deliver at least part of the electrical output stimuli triggered by the pulse-generating circuitry. The implantable pulse generator can further include one or more suture-engagement components, each including one or more holes each having a diameter that is at least 0.1 mm and less than 5 mm.

15 Claims, 13 Drawing Sheets

Related U.S. Application Data

(60) Provisional application No. 62/872,767, filed on Jul. 11, 2019.

(51) Int. Cl.
  *A61N 1/375* (2006.01)
  *A61N 1/378* (2006.01)
(58) Field of Classification Search
  USPC .......................................................... 607/60
  See application file for complete search history.

(56) References Cited

U.S. PATENT DOCUMENTS

| | | | |
|---|---|---|---|
| 5,987,352 A | 11/1999 | Klein et al. | |
| 6,496,715 B1 | 12/2002 | Lee et al. | |
| 6,505,073 B2 * | 1/2003 | Gramse | A61N 1/375 |
| | | | 607/37 |
| 7,554,493 B1 * | 6/2009 | Rahman | A61N 1/37229 |
| | | | 343/702 |
| 7,758,384 B2 | 7/2010 | Alexander et al. | |
| 8,929,986 B2 | 1/2015 | Parker et al. | |
| 8,983,618 B2 * | 3/2015 | Yamamoto | H01Q 1/273 |
| | | | 607/30 |
| 9,511,227 B2 | 12/2016 | Biele et al. | |
| 9,886,002 B2 | 2/2018 | Morioka et al. | |
| 11,097,115 B2 * | 8/2021 | Cong | A61B 17/3421 |
| 2003/0105469 A1 | 6/2003 | Karmon | |
| 2004/0199166 A1 | 10/2004 | Schmieding et al. | |
| 2005/0283170 A1 | 12/2005 | Battles et al. | |
| 2006/0237023 A1 | 10/2006 | Cox et al. | |
| 2006/0247712 A1 * | 11/2006 | Fuller | A61N 1/37229 |
| | | | 607/32 |
| 2008/0015540 A1 | 1/2008 | Muni et al. | |

| | | | |
|---|---|---|---|
| 2008/0076959 A1 | 3/2008 | Farnan et al. | |
| 2008/0097487 A1 | 4/2008 | Pool et al. | |
| 2008/0097496 A1 | 4/2008 | Chang et al. | |
| 2008/0103407 A1 * | 5/2008 | Bolea | A61N 1/37229 |
| | | | 607/42 |
| 2008/0103577 A1 | 5/2008 | Gerber | |
| 2008/0243144 A1 | 10/2008 | Laufer et al. | |
| 2009/0171142 A1 | 7/2009 | Chu | |
| 2009/0182188 A1 | 7/2009 | Marseille et al. | |
| 2009/0248112 A1 * | 10/2009 | Mumbru | A61N 1/37512 |
| | | | 607/60 |
| 2010/0025527 A1 | 2/2010 | Lal et al. | |
| 2011/0288615 A1 * | 11/2011 | Armstrong | A61B 5/0031 |
| | | | 607/2 |
| 2011/0319932 A1 | 12/2011 | Avelar et al. | |
| 2012/0059467 A1 | 3/2012 | Drew et al. | |
| 2012/0283754 A1 | 11/2012 | Murillo et al. | |
| 2013/0085513 A1 * | 4/2013 | North | A61B 17/0485 |
| | | | 606/148 |
| 2013/0238023 A1 | 9/2013 | Wales et al. | |
| 2014/0018885 A1 | 1/2014 | Pianca | |
| 2014/0128955 A1 * | 5/2014 | Howard | A61N 1/36071 |
| | | | 607/117 |
| 2014/0228905 A1 | 8/2014 | Bolea | |
| 2014/0243593 A1 | 8/2014 | Goode et al. | |
| 2014/0246324 A1 | 9/2014 | Baskaran et al. | |
| 2015/0150699 A1 | 6/2015 | Pattison et al. | |
| 2015/0257755 A1 | 9/2015 | North | |
| 2015/0272585 A1 | 10/2015 | Park et al. | |
| 2015/0290465 A1 * | 10/2015 | Mashiach | H02J 50/12 |
| | | | 607/61 |
| 2016/0015988 A1 | 1/2016 | Perryman et al. | |
| 2016/0023012 A1 | 1/2016 | Ries et al. | |
| 2016/0242761 A1 | 8/2016 | Lore et al. | |
| 2016/0262780 A1 | 9/2016 | Kucklick | |
| 2016/0331978 A1 | 11/2016 | Tischendorf et al. | |
| 2017/0202467 A1 * | 7/2017 | Zitnik | A61N 1/3787 |
| 2017/0273733 A1 | 9/2017 | Weber | |
| 2017/0281955 A1 * | 10/2017 | Maile | A61B 5/686 |
| 2017/0281957 A1 * | 10/2017 | Howard | A61N 1/37229 |
| 2018/0071522 A1 | 3/2018 | Feldman et al. | |
| 2018/0085593 A1 * | 3/2018 | Fayram | A61N 1/0551 |
| 2018/0099147 A1 * | 4/2018 | Kane | A61N 1/37518 |
| 2018/0154156 A1 | 6/2018 | Clark et al. | |
| 2018/0185661 A1 | 7/2018 | Imran et al. | |
| 2018/0256906 A1 * | 9/2018 | Pivonka | A61N 1/378 |
| 2018/0264270 A1 | 9/2018 | Koop et al. | |
| 2019/0388696 A1 | 12/2019 | Armesto et al. | |

* cited by examiner

100a 112    135    120    115    110

150

155

125

145

140    130

105    111

100b 160    165

1000—

1002 ⌐
| Provide an enclosure defining a container for housing an electronics assembly |

1004 ⌐
| Couple the header to enclose at a lid of the enclosure |

1006 ⌐
| Connect the communications antenna to an exterior surface of a side wall of the enclosure |

IMPLANTABLE PULSE GENERATOR WITH SUTURE HOLES, METHODS FOR IMPLANTING THE SAME, AND ENCAPSULATION OF EXTERNAL COMPONENTS IN ACTIVE IMPLANTABLE MEDICAL DEVICES

CROSS-REFERENCE TO RELATED APPLICATIONS

This application is a U.S. National Phase Application under 35 U.S.C. § 371 of International Application PCT/US2019/052403, filed Sep. 23, 2019 which claims the benefit of and the priority to U.S. Non-Provisional application Ser. No. 16/140,471, filed on Sep. 24, 2018, and U.S. Provisional Application No. 62/872,767, filed on Jul. 11, 2019. Each of these applications is hereby incorporated by reference in its entirety for all purposes.

FIELD

Embodiments relate to an implantable stimulating device. Specifically, some embodiments relate to an implantable pulse generator device that includes one or more suture holes and/or an antenna with a 2-D form factor.

BACKGROUND

Many biological processes are mediated by intrinsic electrical activity. Occasionally, diseases or medical conditions affect these biological processes and thereby result in irregular or altered electrical activity. Impaired electrical activity can result in cardiac deficits, impaired sensation, deteriorated motor function and even death. Various medical devices have been designed to modify and/or partly control electrical activity, so as to reduce the probability or magnitude of potential symptoms. For example, pacemakers have been used to control the electrical signals of the heart. It would be desirable to develop other medical devices that can precisely stimulate individual nerves and that can placed securely without causing substantial damage to adjacent tissue.

Additionally, implantable medical devices typically include electronics, batteries, antennae, and other active and passive components. These components are hermetically sealed within an enclosure or otherwise encapsulated to prevent moisture ingress. For example, a communications antenna may be attached to the enclosure and the header may be formed in-place by over-molding (e.g., using a biocompatible epoxy to encapsulate the components).

SUMMARY

Various examples are described relating to implantable medical devices, implantable systems, and methods for making implantable medical devices.

In some embodiments, an implantable pulse generator is provided that includes a power source, a wireless communication component configured to facilitate wireless communication with a non-implanted device and pulse-generating circuitry connected to the power source. The pulse-generating circuitry can be configured to identify, based on wireless communication with the non-implanted device, temporal and amplitude characteristics for electrical pulse stimuli and to trigger electrical output stimuli having the temporal and amplitude characteristics. The implantable pulse generation can further include one or more lead connections—each being shaped to engage a lead and electrically connected to the pulse-generating circuitry to enable the lead to deliver at least part of the electrical output stimuli triggered by the pulse-generating circuitry. The implantable pulse generator can further include one or more suture-engagement components, each including one or more holes each having a diameter that is at least 0.1 mm and less than 5 mm.

In some instances, a method for implanting an implantable pulse generator is provided. A trocar can be inserted into a person such that an obturator is near a target anatomical location (e.g., an abdominal muscle). The trocar can include the obturator and a cannula that extends from an opening in the trocar to the obturator. An implantable pulse generator can be inserted into the opening in the trocar to facilitate advancement of the implantable pulse generator through the cannula of the trocar. The implantable pulse generator can include pulse-generating circuitry configured to identify temporal and amplitude characteristics for electrical pulse stimuli and trigger electrical output stimuli having the temporal and amplitude characteristics. The implantable pulse generator can further include one or more lead connections—each shaped to engage a lead and electrically connected to the pulse-generating circuitry to enable the lead to deliver at least part of the electrical output stimuli triggered by the pulse-generating circuitry. The implantable pulse generator can further include one or more suture-engagement components—each including one or more holes. The method can further include positioning a suture grasper device such that a set of grasping jaws of the suture grasper device extend through the cannula of the trocar, tips of the set of grasping jaws are near the target anatomical location, and one or more handle controls remain outside of the opening. The suture grasper device can be configured such that one or more positions of the one or more handle controls control whether the tips of the set of grasping jaws are open or closed. The method can further include controlling the one or more positions of the one or more handle controls across a period of time so as to cause the tips of the set of grasping jaws to facilitate threading a suture through a hole of the one or more holes and an anatomical site at the target anatomical location and to further cause knotting the suture, to thereby at least partly affixed the implantable pulse generator to the target anatomical location.

In some embodiments, a method of manufacturing an implantable pulse generator is provided. The method can include electrically connecting each of one or more lead connections with pulse-generating circuitry, where the pulse-generating circuitry is configured to identify temporal and amplitude characteristics for electrical pulse stimuli and trigger electrical output stimuli having the temporal and amplitude characteristics. The method can also include making or securing one or more external surfaces such that the pulse-generating circuitry is within the one or more external surfaces, wherein the one or more external surfaces includes or is further processed to include: one or more holes each having a diameter that is at least 0.1 mm and less than 5 mm.

In some embodiments, one general aspect includes an implantable device, including: an enclosure including a lid and a side wall connected to the lid. The implantable device also includes an electronics assembly disposed within an interior volume of the enclosure. The implantable device also includes a set of conductive leads electrically connected to the electronics assembly and extending through the enclosure. The implantable device also includes a communications antenna disposed on an exterior surface of the side wall and including a main body and a tab, the tab including a set of conductive terminals, where the main body is coated in a bio-compatible material and the set of conductive terminals is electrically connected to the set of conductive leads.

In some embodiments, another general aspect includes a method, including: providing an enclosure including an electronics assembly. The method also includes coupling a header to enclose at least a lid of the enclosure, where an access window is formed at a perimeter edge of the header and a set of conductive leads extend from the electronics assembly and through the access window. The method also includes connecting a communications antenna to an exterior surface of a side wall of the enclosure. The communications antenna including a body and an electrical termination tab that corresponds in size and shape to the access window and aligns a set of conductive terminals disposed in the electrical termination tab with the set of conductive leads.

In some embodiments, another general aspect includes a system, including: an implantable medical device and an antenna. The implantable medical device also includes an enclosure to house an electronics assembly, the enclosure including a lid and a side connected to the lid. The implantable medical device also includes a set of conductive leads to extend from the electronics assembly to outside the enclosure via the lid. The antenna connects to an exterior surface of the side at a mounting location. The antenna includes a body portion encased in a bio-compatible material, a tab portion connected to the body portion, and a set of conductive terminals disposed in the tab portion and that align with the set of conductive leads when the antenna is connected to the exterior surface at the mounting location.

In some embodiments, another general aspect includes a device, including: an enclosure including a lid and a side wall. The device also includes an electronics assembly disposed within an interior volume of the enclosure and including a plurality of conductive leads that extend through the lid of the enclosure. The device also includes one or more electrical components connected to an exterior surface of the lid and electrically connected to a first portion of the plurality of conductive leads. The device also includes a header that encapsulates the one or more electrical components and includes an access window through which extends a second portion of the plurality of conductive leads. The access window is sized to receive a tab of a communications antenna.

In some embodiments, another general aspect includes a device, including: an enclosure for housing an electronics assembly. The enclosure includes a lid and a side wall connected to the lid. The device also includes a set of conductive pins extending through the lid of the enclosure. The device also includes a communications antenna connected to an exterior surface of the side wall, the communications antenna including a set of conductive terminals. The set of conductive pins is received by and electrically connected to the set of conductive terminals.

BRIEF DESCRIPTION OF THE DRAWINGS

Illustrative embodiments of the present invention are described in detail below with reference to the following drawing figures.

DESCRIPTION

Figure 1A:
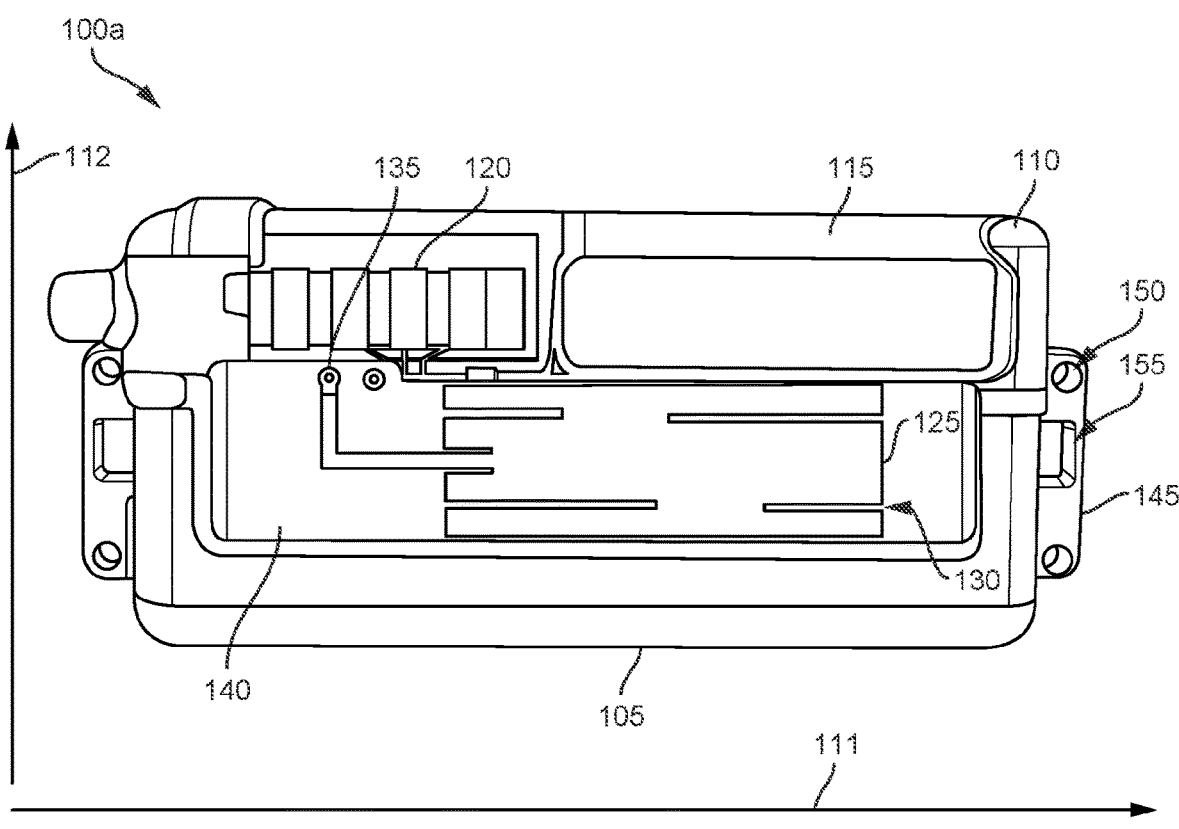
FIG. 1A-1B show multiple views of an implantable pulse generator according to an embodiment of the invention.

Examples are described herein in the context of implantable medical devices such as implantable pulse generators ("IPGs") or other such devices for neuromodulation. Those of ordinary skill in the art will realize that the following description is illustrative only and is not intended to be in any way limiting. For example, the features described with respect to the implantable medical devices are applicable to any other medical device that is implanted into a person's body. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

Implantable devices have the potentially to directly affect very specific parts of the body. However, both implantation process and the maintained internal positioning of the implantable device is associated with substantial risks. For example, during the implantation process, surrounding tissue may be damaged. As another example, after the device is implanted, the surrounding area may become inflamed. As yet another example, after the device is implanted, it may move from a target location, which may cause further tissue damage and/or inflammatory responses. Thus, it would be desirable to configure a device and implantation process to reduce the risk of tissue damage, inflammatory response and device movement.

In some embodiments, components and spatial features of the implantable device can facilitate reducing these risks. For example, incorporating suture-engagement components in the device (e.g., one or more tabs, hooks, holes, channels, etc.) can facilitate implanting the device through a smaller pathway (and/or while contacting fewer anatomical structures) and/or can facilitate stably securing the device at a target location. A suture-engagement component can include or can have a planar shape, a flat surface, a rounded surface (e.g., at an edge) and/or a wrapped surface (e.g., a c-shaped surface, which may wrap around one or more internal parts of the implantable device). A suture-engagement component can be rigid and can include (for example) a metallic material, a metal, titanium and/or a polymer. In some instances, a suture-engagement component includes a same material as included in a housing of the implantable device. In some instances, a composition of a suture-engagement component is the same as a housing of the implantable device. In some instances, a suture-engagement component is an extension of or is part of a housing of the implantable device.

A suture-engagement component may be located such that at least part of the suture-engagement component is part of an outer surface of the implantable device. For example, the suture-engagement component may include a tab, protrusion, edge, hook, J-shaped or L-shaped edge, etc. of the device. The suture-engagement component may have a thickness that is different than (e.g., smaller than or larger than) a median, mean, maximum or center thickness of the device. In some instances, the suture-engagement component may have a thickness that varies across a dimension of the device (e.g., to make a ridge or edge around the device or to taper the thickness across the suture-engagement component). The differential thickness (e.g., within the suture-engagement component and/or relative to another part of the device) can facilitate implanting the device, as it can facilitate grasping the structure, hooking the structure, and so on with a surgical tool. As one particular example, a configuration that includes a protruding thin surface can facilitate implanting the device by gripping (using a surgical tool) the thin surface and pulling or pushing the device to a target location, rather than gripping a wider portion of the device (e.g., which may involve opening the gripping tool wider, which can cause increased damage).

A device may include a single suture-engagement component or a set of suture-engagement components (e.g., two or four suture-engagement components). When a device includes multiple suture-engagement components, the suture-engagement components may be positioned in same, similar or complementary configurations. For example, in instances in which each suture-engagement component includes one or more layers, the suture-engagement components may be configured such that the one or more layers of one suture-engagement component are parallel to (and/or in a same plane as) the one or more layers of each other suture-engagement component.

The suture-engagement component can include one or more holes. The hole(s) can be sized to be large enough to receive a suture. For example, each hole can have a diameter that is at least 0.1, 0.5, 1 or 2 mm. The diameter may be less than (for example) 10 mm, 5 mm, 3 mm or 2 mm (e.g., to facilitate compact design). Upon positioning an implantable location near a target location, the hole(s) can be used to secure the device to the target location. For example, with respect to each of the one or more holes (or a subset thereof) a suture may be threaded through the hole and also threaded through an anatomical structure (e.g., a tissue).

Each hole of the one or more holes may extend through the device along a thickness dimension. Thus, for example, if the suture-engagement component is a single layer, the hole may extend through the layer; if the suture-engagement component includes multiple layers, the hole may extend through each of the multiple layers. Thus, in some instances, the hole includes a channel (e.g., through one or more layers). The suture-engagement components may be positioned or defined such that the implantable device includes holes at opposite sides of the device. For example, one or more holes can be positioned near a first edge of the device (e.g., such that a center of each of the one or more holes is within 20, 10, 5 or 3 mm from the first edge), and one or more other holes can be positioned near a second opposite edge of the device (such that a center of each of the one or more other holes is within 20, 10, 5 or 3 mm from the second opposite edge). In some instances, the implantable device includes at least four holes. In some instances, at least two holes are separated along a length-wise dimension by at least 80%, at least 90% or at least 95% of a length of the device. In some instances, at least two holes are separated along a width-wise dimension by at least 80%, at least 90% or at least 95% of a width of the device.

The implantable device can include an implantable pulse generator. The implantable pulse generator can include pulse-generating circuitry that controls pulses output in connection with the device. For example, the pulse-generating circuitry can be configured to identify temporal and/or amplitude characteristics for pulse stimuli that are to be output by one or more leads that are to be connected to the implantable device. In some instances, the pulse-generating circuitry generates triggers of pulses and/or a time-series stimulation electrical output (e.g., to be delivered to one or more leads). The implantable device can include one or more lead connections (e.g., one or more ports)—each of which can be configured (e.g., shaped and positioned) to physically engage or attach to a lead and electrically connect the lead to the pulse-generating circuitry. The implantable device can further include a power source (e.g., a rechargeable or non-rechargeable battery). The implantable device can also include a wireless communication component to facilitate communication (e.g., via a Bluetooth channel) between the implantable device and another device. The other device can include a non-implanted and/or remote device. The wireless communication component can include an antenna.

As another example of an implantable-device feature that can reduce implantation risks, efficient configuration of the wireless communication component can reduce a size of an implant, so as to reduce the extent to which an implantation process and/or the implantable device's final position affects various anatomical features. For example, the wireless communication component can include an antenna that includes a planar component that is positioned on an external surface of the implantable device. The antenna may be (for example) placed on the can housing. The planar component can include (for example) a conductive material that is of a shape that enables the antenna to transmit and/or receive signals at a target frequency or target frequency range. The shape can include (for example) a square, rectangular, circular or oval shape that can be patterned to (for example) include a set of slots and/or openings at which the conductive material is absent. The antenna can include a 2-D form factor. The slots and/or openings may have an edge or portion of a perimeter that is at a perimeter of the shape. The planar component can be connected (e.g., via a wire) to circuitry (e.g., pulse-generating circuitry) within the implantable device. The connection can (for example) enable the other device to send commands that specify or constrain pulse characteristics of pulses generated by the pulse-generating circuitry.

In some instances, the wireless communication component includes multiple planar components that are separated by an insulating layer (e.g., and connected via a wire). One of the planar components (e.g., a non-external component) can serve as a ground. Thus, the wireless communication component can include a stack, which may be positioned on a housing of the implantable device. The implantable device can (in some instances) include a can housing that houses (for example) pulse-generating circuitry and a power source (e.g., a rechargeable battery) and a header housing (e.g., a header coating) that houses (for example) one or more lead connections and a coil (e.g., for recharging the battery). The coil can include (for example) a conductive wire, such as a gold wire that has multiple turns. For example, the coil may include at least 3, at least 5 or at least 8 turns and/or less than 20, less than 15, or less than 10 turns. A diameter of the turns may be (for example) at least 10 mm, at least 20 mm or at least 50 mm and/or less than 200 mm, less than 100 mm or less than 75 mm. Additional configuration details for potential IPG coils are disclosed in U.S. Application No. 62/730, 104, filed on Sep. 12, 2018, which is hereby incorporated by reference in its entirety for all purposes. The wireless communication component can be positioned at least partly on or fully on the can housing and/or at least partly on or fully on the header housing.

In an illustrative example, an implantable medical device includes its active components (e.g., electronics and battery) either housed within a metal enclosure or encased in an epoxy header. The epoxy header includes an access window by which conductive leads from the active components are accessible. A communications antenna, which is made in a ceramic substrate, is fully or partially encapsulated in epoxy as part of a separate process and connected to an exterior surface of the metal enclosure and apart from the header. A tab located at a top of the antenna includes conductive terminals which are mated with the conductive leads during assembly. The size and shape of the tab is made to have a corresponding shape as the access window, but with slightly smaller dimensions to ensure that the tab fits within the access window. Once mated, the conductive leads are electrically connected with the conductive terminals using a laser welding process or other suitable process. A silicone or other bio-compatible material is then applied to fill in the access window. A bead of this material is also applied between a perimeter edge of the antenna that is adjacent the header and the header to create a smooth transition between the antenna and the header.

Conventional over-molding of header components may prove challenging because of the complicated fixture needed to hold all components in place during molding, the additional time required for epoxy to surround all components, and the additional time required for curing The described arrangement, however, reduces the amount of time needed for flowing epoxy around a complicated geometry on the top of the header and reduces the amount of cure time for the epoxy header as compared to headers that enclose communications antennas. Additionally, because of the simpler geometry on the top of enclosure, pre-molded headers may be practical, which may reduce production costs and production time. Because the communications antenna and the header are made using different processes, a designer can select customized epoxies with different properties for the communications antenna as compared to the header (e.g., one for the header and a different one to encapsulate the antenna). Making the communications antenna separate from the header also enables improved uniformity of the thickness of the epoxy. This ensures a more predictable operation of the communications antenna, which could be impacted by un-uniform surfaces. Making the communications antenna separate from the header allows for a full cure cycle of the communication antenna because the antenna does not include any active components that could be harmed during the cure cycle. Finally, connecting the communications antenna to an exterior surface of the enclosure as described allows the antenna and the implantable medical device (without the antenna) to be manufactured in parallel, thereby obtaining the benefits of parallelization.

Figure 1B:
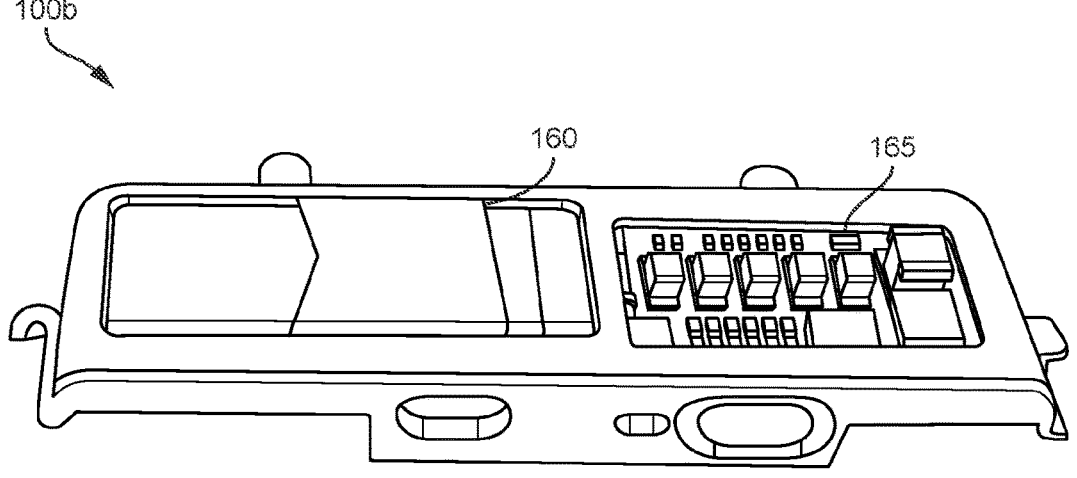

FIG. 1A-1B show multiple views of an implantable pulse generator according to an embodiment of the invention. FIG. 1A shows a front side 100a of the implantable pulse generator. The implantable pulse generator includes a can 105 and a header 110. The implantable device can be characterized as having a length along a length dimension 111, a width along a width dimension 112 and a depth along a depth dimension (perpendicular to each of length dimension 11 and width dimension 112). The length of the device may be (for example) less than 3 inches, less the 2 inches or less than 1 inch. The width of the device may be (for example) less than 2 inches, less than 1 inch or less than 0.5 inch. Can 105 and header 110 can correspond to different portions of the width of the device.

Can 105 includes a housing that houses various components, but also can collectively refer to the can housing and the components housed within the can housing. The can housing can include a metal, such as titanium. The can housing can house (for example) circuitry (e.g., pulse-generating circuitry) and a rechargeable battery. The can housing (e.g., and the implantable device itself) can be hermetically sealed.

Header 110 can include a header housing (e.g., a coating) that houses various components, but also can collectively refer to the header housing and components housed within the header housing. The header housing can include an epoxy or polymer. The header housing can house (for example) a charging coil 115 that is connected to the rechargeable battery and one or more lead connections (e.g., a connector stack 120). Each component (or portion of a component) of the implantable pulse generator that is part of an external surface of the implantable device (e.g., the can housing, the header housing) can be biocompatible.

The implantable device can further include a wireless communication component, such as an antenna 125. The antenna 125 can include (for example) a BLE antenna. The antenna can include a solid conductive material, in which a set of slots 130 protrude. The quantity, locations, widths and lengths of the slots in the set can influence to which frequency the antenna 125 is tuned. Antenna configurations are further described in U.S. application Ser. No. 15/969, 976, filed on May 3, 2018, which is hereby incorporated by reference in its entirety for all purposes. In some instances, the antenna is configured to have an elliptical polarization, such that emitted fields have elliptical polarization.

The conductive material can extend to connect to one or more vias 135 (or feedthroughs). A via 135 can connect antenna 125 to circuitry, such as pulse-generating circuitry, such that a received signal can influence pulse characteristics. A via 135 can further connect antenna 125 to a ground. In some instances, a can housing can serve as a ground. The wireless communication component may then include (for example) a first conductive layer that is in contact with (e.g., on and/or bonded to) the can housing, a second conductive layer that is part of an external surface of the implantable device, an insulating and low-loss layer 140 (e.g., a ceramic layer or dielectric layer) that is between the first and second conductive layer, a first via that connects the second conductive layer to circuitry inside the can housing, and a second via that connects the second conductive layer to the first conductive layer.

The implantable device can also include one or more suture-engagement components 145, which can include one or more edge portions of the implantable device. A suture-engagement component 145 can be (for example) part of or attached to (e.g., via welding) a can housing. For example, a suture-engagement component 145 can be welded to or monolithic with the can housing. In one instance, suture-engagement component 145 can include a metal (e.g., titanium) tab that extends out of a curved portion of can housing. Each suture-engagement component 145 can include one or more holes, such as a one or more suture-engagement holes 150 and one or more other holes 155. Each suture-engagement hole 150 may be sized to be large enough to allow a suture to be threaded through it (e.g., having a diameter that is at least 2, 5 or 10 times that of a suture) but size constrained (e.g., having a diameter that is less than 30, 20 or 10 times that of a suture) so as to constrain movement of the suture after the implantable device is implanted and sutured to an anatomical site. Each of the one or more other holes 155 may (for example) be larger in diameter than the suture-engagement holes 150. During an implantation process, a surgical tool may engage (e.g., may hook, grasp, etc.) the other hole to facilitate pulling or pushing the implantable device to a target location or target position.

FIG. 1B shows internal components 100b of the implantable pulse generator.

Internal components 100b may be positioned within a can housing. Internal components 100b can include a rechargeable battery 160 and circuitry 165. Circuitry 165 can include (for example) over 100.000, over 200.000, or over 500.000 transistors; over 500,000, over 750,000 over 1,000,000 connections; and/or a sleep current than is less 1 μA, less than 2 μA, or less than 1 μA. Circuitry 165 can include a modular design.

Circuitry 165 can include battery charging and communication circuitry, which can monitor and control currents and voltages supplied to the battery. The battery charging and communication circuitry can further monitor a charge of the battery. The battery charging and communication can further receive and effect emergency wireless commands (e.g., received initially at the antenna and muted to the battery charging and communication circuitry) to (for example) reset, stop or resume stimulation.

Circuitry 165 can include monitoring circuitry that measures impedance of one or more stimulating electrodes and that monitors the status of stimulation. For example, the impedance can be measured using sub-threshold pulses (e.g., 10 μs, <100 μA). As another example, high-resolution stimulation waveforms can be detected and characterized to track the status of stimulation. Device-internal voltage or current measurements can also be accessed and characterized. The monitoring circuitry may (for example) locally evaluate one or more rules using the monitored data and/or may cause the monitored data to be transmitted to another device. For example, a rule may include a condition that is satisfied upon detecting that a stimulation waveform has a given property (e.g., an amplitude or frequency that exceeds a threshold) and/or that an impedance has a given property (e.g., exceeding a threshold that may be fixed or dependent on a stimulation parameter). When the condition is satisfied, the monitoring circuitry may cause a stimulation parameter to be changed and/or an alert signal to be transmitted.

Circuitry 165 can include stimulation (e.g., pulse-generating) circuitry. The stimulation circuitry can identify an amplitude, temporal pattern and/or current steering for stimulation. The stimulation circuitry can trigger and define (for example) low-frequency stimulation and high-frequency block (e.g., 1 Hz-50 kHz).

Internal components 100b can further include (for example) one or more sensors (e.g. an accelerometer), memory (e.g., a flash memory), a communication control (e.g., BLE matching circuitry), wireless power transfer (WPT) matching circuitry, one or more inductors (e.g., to generate high voltages for an integrated circuit including various circuitry), one or more micro-processing units (e.g., with Bluetooth capability) and/or a fusible resistor. For example, the memory may be used to store an event log and/or back-up firmware images.

Figures 2A, 2B:
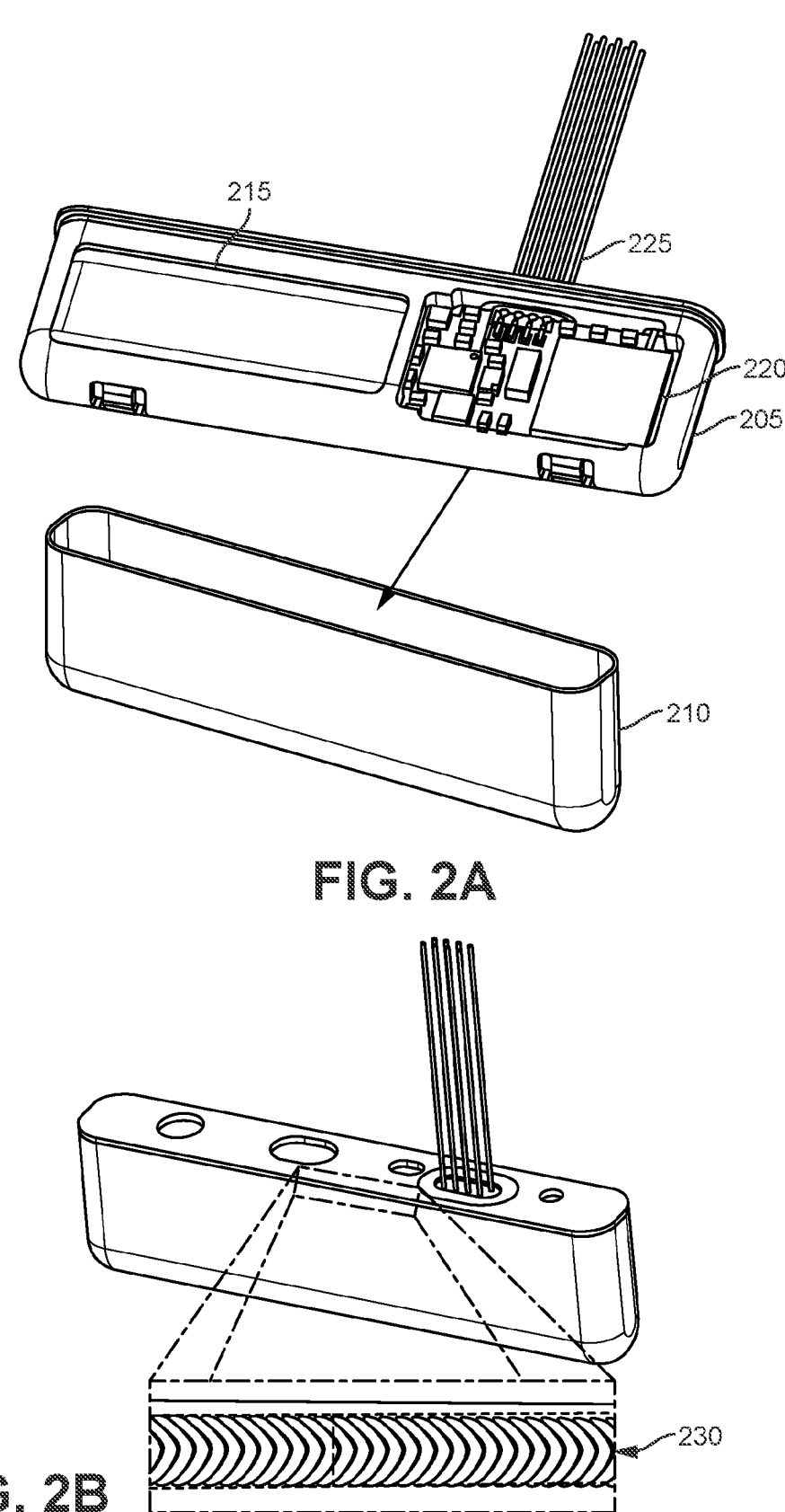
FIGS. 2A-2E show various stages during a process of manufacturing an implantable pulse generator according to an embodiment of the invention.

FIGS. 2A-2E show various stages during a process of manufacturing an implantable pulse generator according to an embodiment of the invention. In FIG. 2A, internal components 205 are positioned within a can housing 210. FIG. 2B shows internal components 205 positioned within can housing 210. Internal components 205 can include (for example) various components as disclosed herein (e.g., components described in relation to FIG. 1B). For example, internal components 205 can include a rechargeable battery 215 and a printed circuit board array 220 that includes various circuitry (e.g., pulse-generating circuitry). A set of connections 225 can connect to various circuitry in printed circuit board array 220 can extend out of a top surface of internal components 205 such that they are at least partly located outside of can housing 210 subsequent to positioning of internal components 205 within can housing 210.

Upon having positioned internal components 205 within can housing 210, a securing process can be performed to inhibit or prevent relative motion of internal components 205 and can housing 210. For example, a top perimeter of can housing 210 can be welded to a top perimeter of internal components, as illustrated in an exploded perimeter view 230 in FIG. 2B.

Figure 2C:
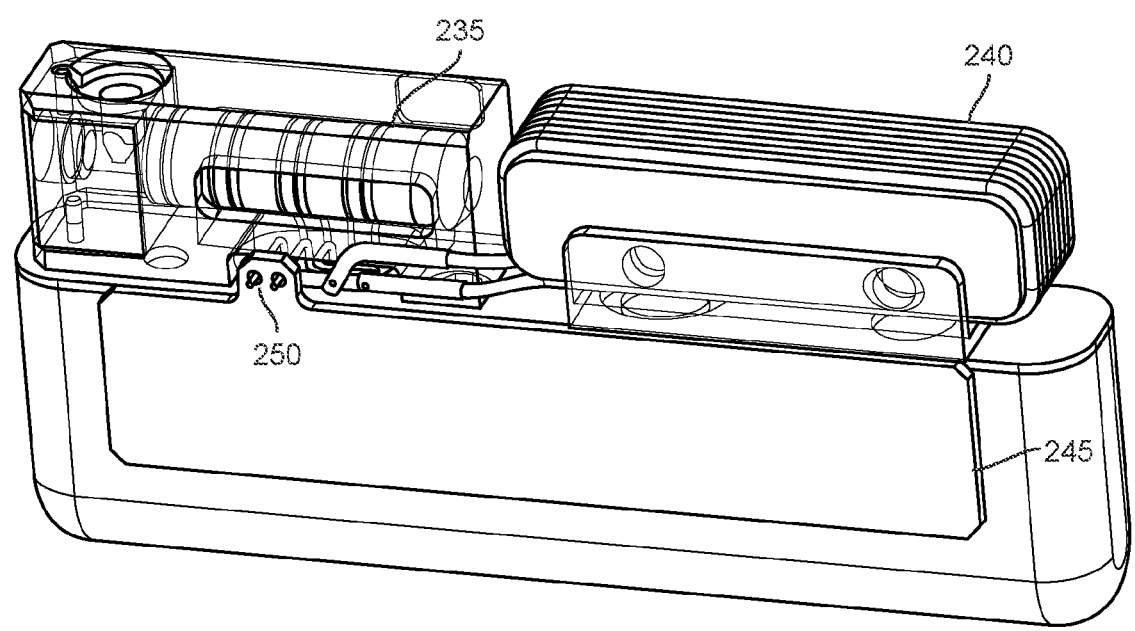

Header components can be positioned on a top surface of the housed internal components, as illustrated in FIG. 2C. The header components can include a coil 235 (e.g., to receive power from an external powering device and to avail the power via a connection to the battery) and one or more lead connections 240. One or more lead connections 240 can include a bond connector stack.

Further, an antenna 245 can be attached to (e.g., bonded to) on an outside of can housing 210. Contacts 250 of the antenna can be welded to one or more vias (e.g., to connect antenna 245 to circuitry and to a ground.

Each connection of set of connections 225 can be connected to a header component. For example, one or more of set of connections 225 can connect with lead connections 240, such that stimulation parameters (or stimulation voltage time series or triggers) can be communicated from circuitry housed in can housing 210 to lead connections 240. As one (additional or alternative) example, a connection of set of connections can connect to coil 235, such that power from coil 235 can be availed to rechargeable battery 215. Connecting set of connections 225 to one or more header components can include (for example) welding an end of each connection to a contact corresponding to a header component.

Figure 2D:
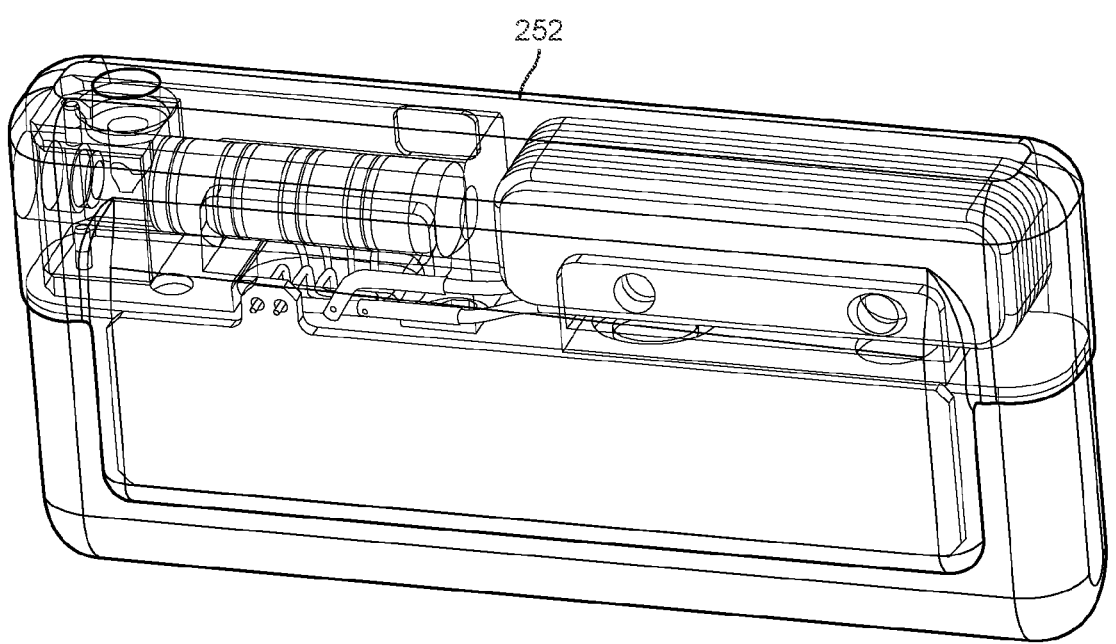

A header housing can be formed by applying (e.g., pouring) a header-housing material (e.g., a non-conductive material). For example, an epoxy material can be poured into a mold (e.g., that includes the header components positioned on the top surface of the housed internal components. The epoxy can then be cured to harden. FIG. 2D shows the header housing 252, which houses the header components. In some instances, the epoxy material covers the antenna. In some instances, a second pour of epoxy is used to cover the antenna in a separate process.

Figure 2E:
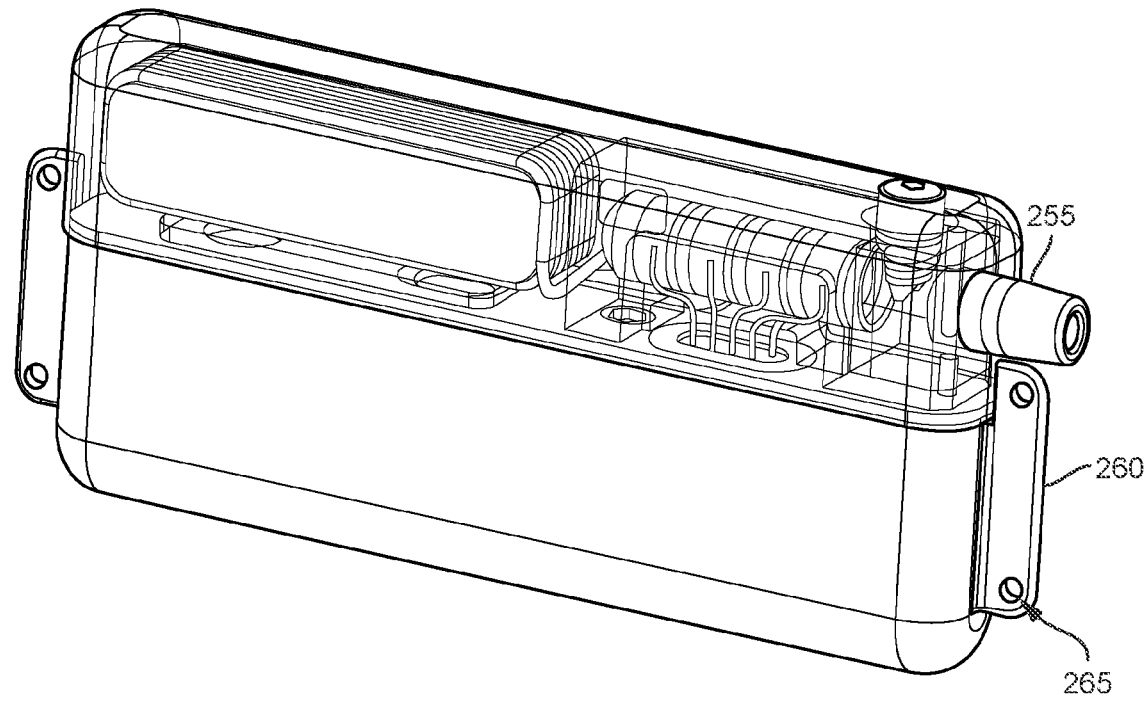

As shown in FIG. 2E, a silicone lead support 255 can be bonded to header housing 252. Silicone lead support 255 can be shaped to support and/or engage a lead, such that it can be connected to one or more lead connections 240 during an implantation process.

Further, a set of suture-engagement components 260 are attached to housing of the device. In this instance, an edge of each suture-engagement component 260 is laser welded to can housing 210. Each suture-engagement component 260 includes a set of holes 265 to receive a suture. It will be appreciated that alternative manufacture techniques are contemplated. For example, a can housing can be configured to include one or more holes 265. As another example, a suture-engagement component 260 can be bonded to the header housing instead of or in addition to securing suture-engagement component 260 to can housing 210.

Figure 3A:
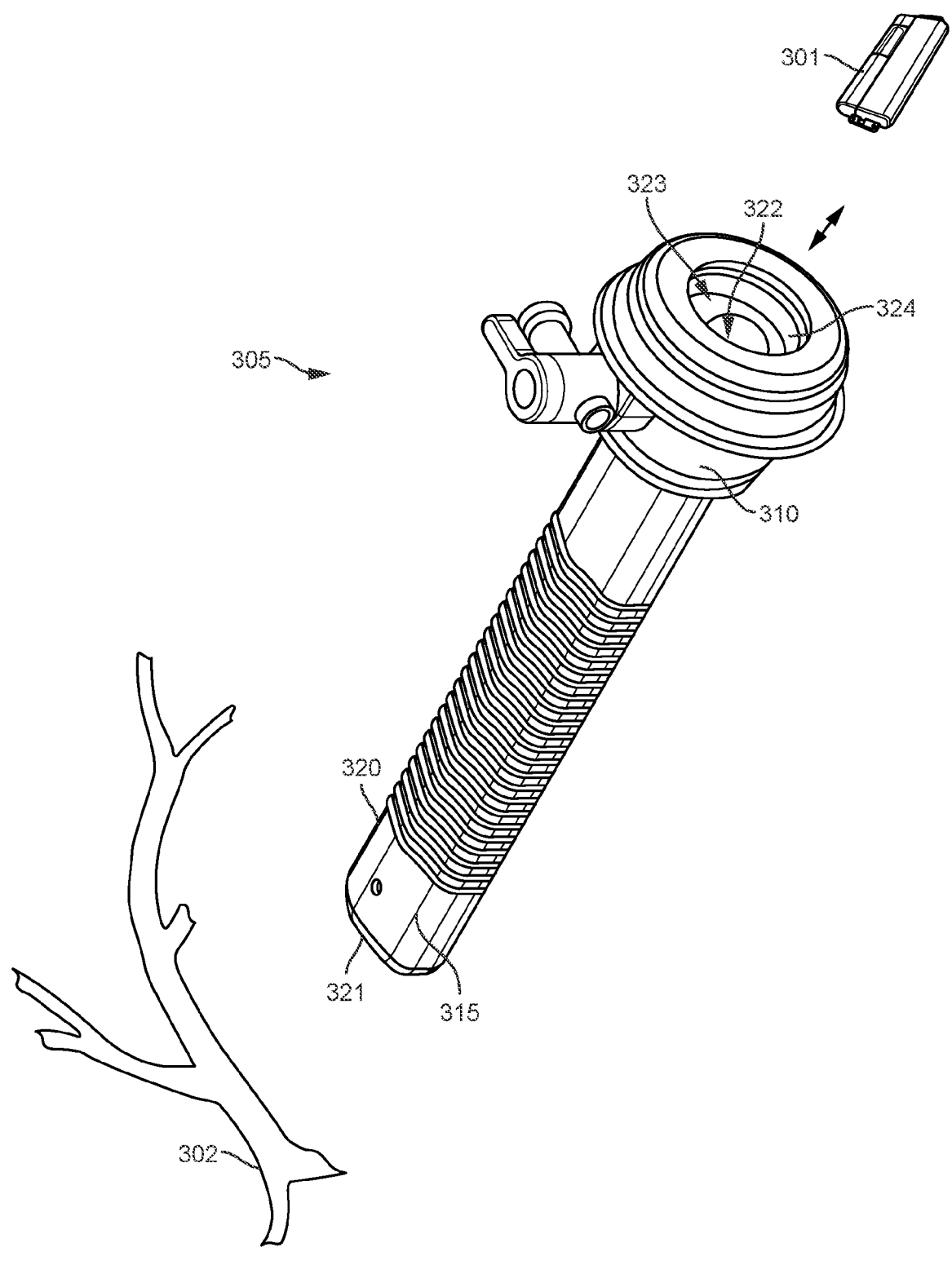
FIGS. 3A-3C illustrate various stages during a process of implanting an implantable pulse generator according to an embodiment of the invention.
Figure 3B:
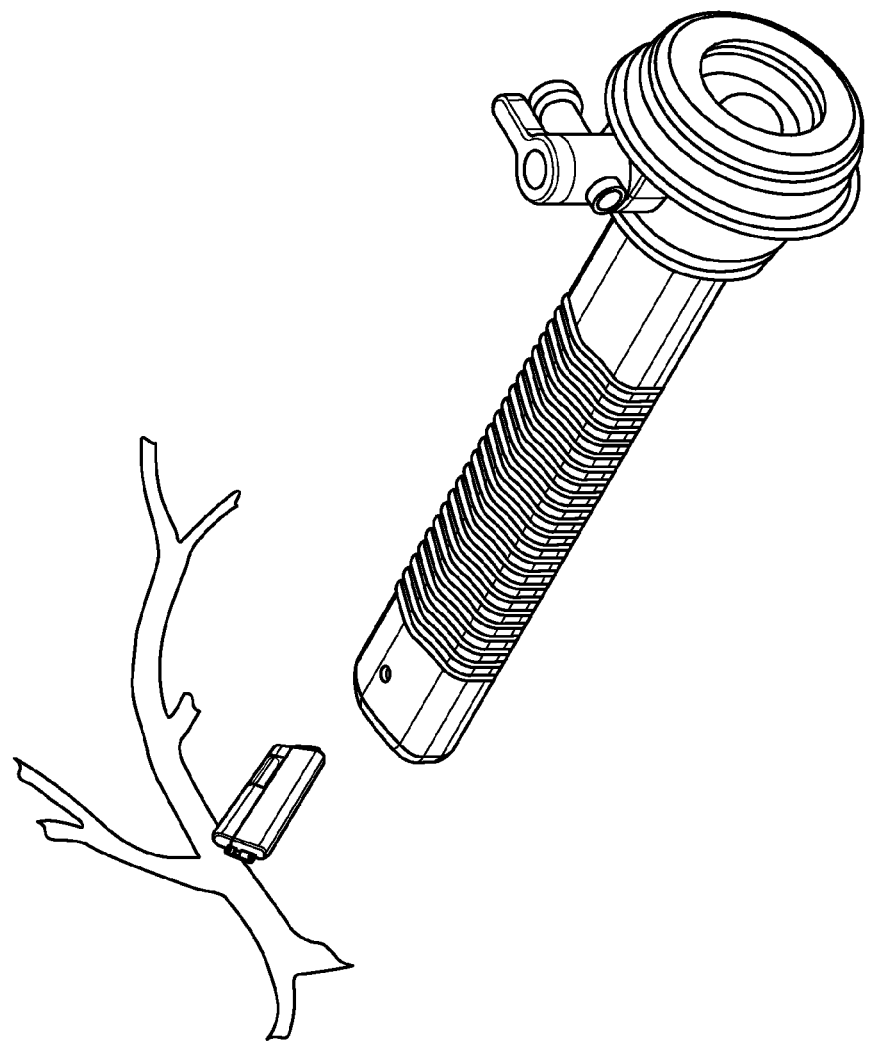
Figure 3C:
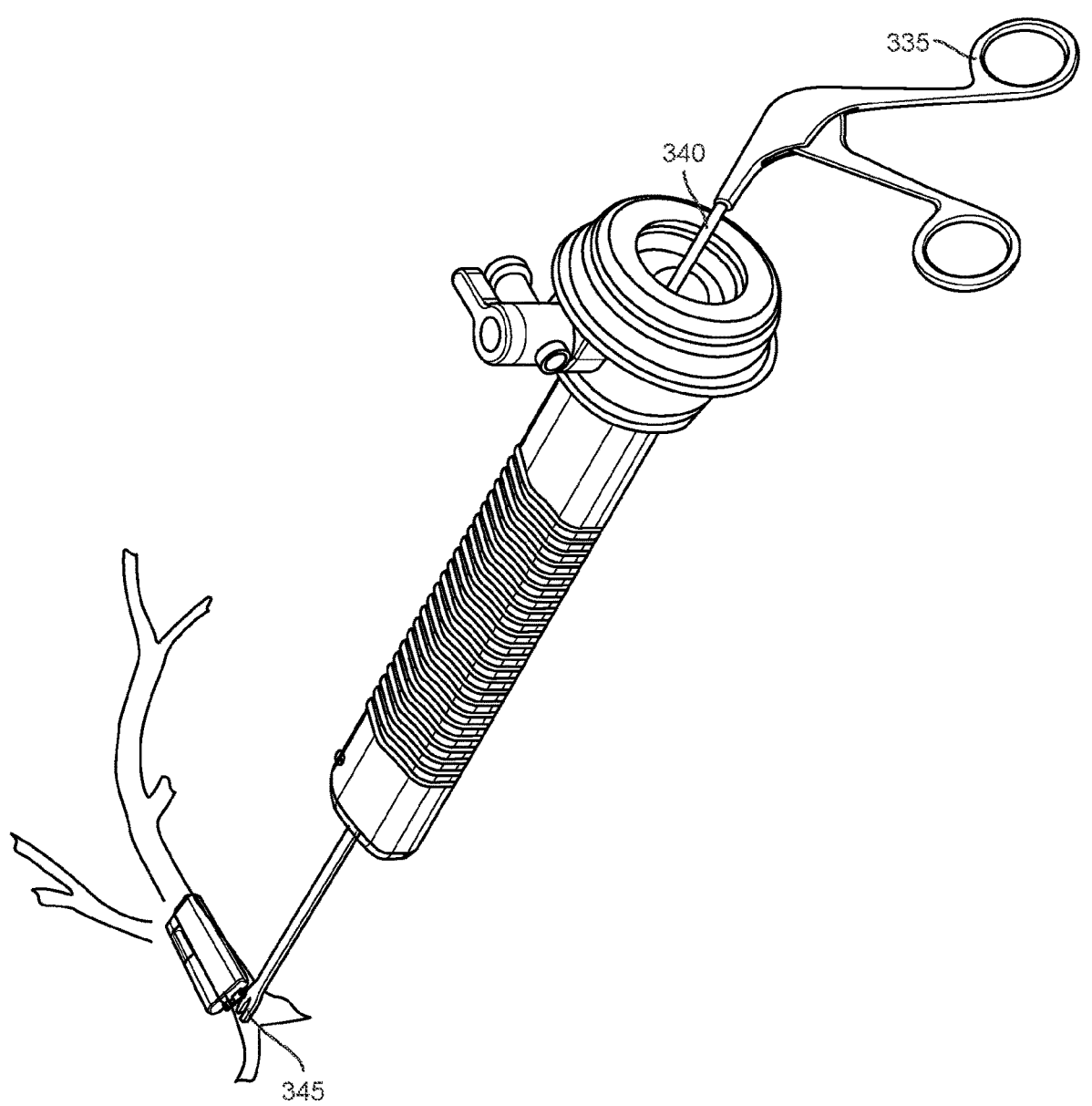

FIGS. 3A-3C illustrate various stages during a process of implanting an implantable pulse generator according to an embodiment of the invention. In some instances, an implantable device 301 can be moved to a target destination (e.g., near or at a target biological structure 302) by inserting implantable device 301 into a trocar 305. Trocar 305 can include a detachable obturator assembly (that includes an obturator housing, an obturator tip and an obturator body) (not pictured), a cannula assembly (that includes a cannula housing 310 and a cannula sleeve 315). The cannula assembly can include two or more openings to facilitate movement of various devices or parts of devices through cannula sleeve 315. Specifically, the cannula assembly can include a distal opening 321 of a sleeve body 320, a proximal opening 322 of sleeve body 320, a distal end opening 323 of cannula housing 310, and a proximal opening 324 of cannula housing 310. Distal opening 321 of sleeve body 320 can be configured to attach (e.g., and detach) from the obturator body. The obturator assembly can be used to pierce through tissue to advance an edge of the trocar towards a target location.

A sequence of actions to be performed to position the trocar near a target location, as detailed in U.S. Provisional Application 62/669,485, filed on May 10, 2018, which is hereby incorporated by reference in its entirety for all purposes. For example, an incision can be made in a person's skin. The obturator assembly can be inserted through the incision. As the obturator assembly is advanced to a target location, the obturator tip dissects tissue to allow for movement of the trocar. The attached cannula assembly follows through the dissected portion. In some instances, when the obturator assembly reaches a location near a target location, the obturator assembly can be removed from cannula assembly, leaving the cannula assembly embedded through the tissue to function as a laparoscopic port to a target site.

One or more surgical instruments (e.g., one or more laparoscopic tools) can then be inserted into a proximal opening 322 of sleeve body 320 and extended through sleeve body 320, such that one or more ends of the surgical instrument(s) pass through a distal end 323 of cannula housing 310. The instruments may be used for manual dissection of biological structures to create a pathway to the target biological structure. For example, graspers can be inserted through one or more of cannula assemblies to move or dissect biological structures along natural tissue planes to provide a pathway to access the target biological structure. In other embodiments, graspers, dissectors, scissors, retractors, etc., are placed through the one or more of cannula assemblies for manipulations of the operative field or target biological structure by the user, e.g., a surgeon. Once the pathway is created, the one or more surgical instruments may be removed from the cannula assembly.

As shown in FIG. 3A, implantable device 301 can then be delivered through the cannula assembly into a target site of the target biological structure. In various embodiments, after the pathway is created to the target biological structure (and optionally a guidewire is inserted), implantable device 301 is fed through the cannula assembly into the target site. In some instances, implantable device 301 is introduced over a guidewire and guided through the cannula assembly and delivered into the target site. (FIG. 3B.) Additionally or alternatively, a lead assembly may be introduced over the guidewire and guided through the cannula assembly into the target site and delivered to the site of target biological structure 302. Implantable device 301 and a lead assembly may be delivered through the cannula assembly at the same time or separate from one another depending on the circumstances and type of neuromodulation system being used for therapy. For example (e.g., in an instance where the lead assembly is removable from implantable device 301), implantable device 301 may be delivered and implanted in the target site, and subsequently the lead assembly may be delivered, attached to target biological structure 302 and physically and electrically connected to implantable device 301.

As shown in FIG. 3C, a surgical instrument 330 can then be placed at least partly through the cannula assembly. Surgical instrument 330 can include one or more controls (e.g., handles 335), an extended portion 340 (e.g., having a width less than a width of sleeve body 320), and one or more distal controllable features 345. Surgical instrument 330 can be inserted into the cannula assembly such that one or more distal controllable features 345 fully traversed through sleeve body 320 and exited distal opening 321 of sleeve body 320, while the one or more controls remain outside of proximal opening 324 of cannula housing 310.

Surgical instrument 330 can be configured for manual manipulation of implantable device 301 and tissue within the target site to implant the implantable device 301 within the target site. For example, graspers can be inserted through one or more of cannula assemblies to move implantable device 301 and one or more sutures to attach implantable device to target biological structure 302. Surgical instrument 330 can include (for example) graspers. Distal controllable features 345 can be configured to open or close relative to each other in response to opening or closing of handles 335.

In some instances, one or more controls of surgical instrument 330 can be manipulated to cause one or more distal controllable features 345 to grasp a part (e.g., a suture-engagement component) of implantable device 301 to move and/or orient implantable device 301 in a desired location and/or desired position (e.g., corresponding to a location and/or position of target biological structure 302). One or more controls of surgical instrument 330 can further be used to cause one or more distal controllable features 345 to thread a suture through each of one, more or all holes (e.g., in each of one, more or all suture-engagement components) in implantable device 301 and through a part of target biological structure 302 and to knot the suture. For example, one or more distal controllable features 345 can grasp a needle attached to a suture and thread the needle through a hole in implantable device 301 and through a part of target biological structure 302. Surgical instrument 330 can be controlled so as to (for example) sequentially thread each of multiple sutures through an individual hole in implantable device 301 and a distinct position at target biological structure 302. In some instances, implantable device 301 can be secured to a target biological structure via at least or exactly two holes in implantable device 301 or via at least or exactly four holes in implantable device 301.

In some instances, one or more sutures and/or one or more needles are inserted to the target site through a cannula assembly of trocar 305. In some instances, one or more sutures and/or one or more needles are inserted to the target site through another cannula assembly of another trocar (e.g., the other cannula assembly being positioned such that a distal opening of the cannula assembly is within the target site and near the distal opening of the cannula assembly of trocar 305). In some instances, multiple surgical instruments are used to suture implantable device 301 to target biological structure 302 (e.g., each of which may be positioned through a different trocar). Upon having knotted a suture, the suture may be separated from a needle (e.g., by cutting the suture), and the needle may be subsequently removed from the target site (e.g., by grasping the needle using a surgical instrument and removing one or more distal controllable features 345 from trocar 305).

In instances in which implantable device 301 is not attached to a lead assembly prior to implantation and/or insertion through a trocar, a same or different surgical instrument can be used to connect one or more first ends of the lead assembly to implantable device 301 (e.g., after or before implantable device 301 is sutured to target biological structure). In some instances, a same or surgical instrument (e.g., and/or one or more same or different trocars) can be used to attach one or more second ends to one or more other target biological structures (or one or more other parts of target biological structure 302).

Upon having securely anchored each of implantable device 301 and the lead assembly, each cannula assembly and each surgical instrument (and optionally the guidewire) used in the process can be removed from the surgical site. Specifically, each surgical instrument (e.g., surgical instrument 330) and any guidewire can each be removed via a cannula assembly, and each trocar or cannula assembly can then be removed from the laparoscopic port(s). In some embodiments, the laparoscopic ports are closed using sutures, staples, or similar closing devices. Implantable device 301 remains implanted within the target site and the lead assembly remains attached to the target biological structure.

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments.

Figure 4:
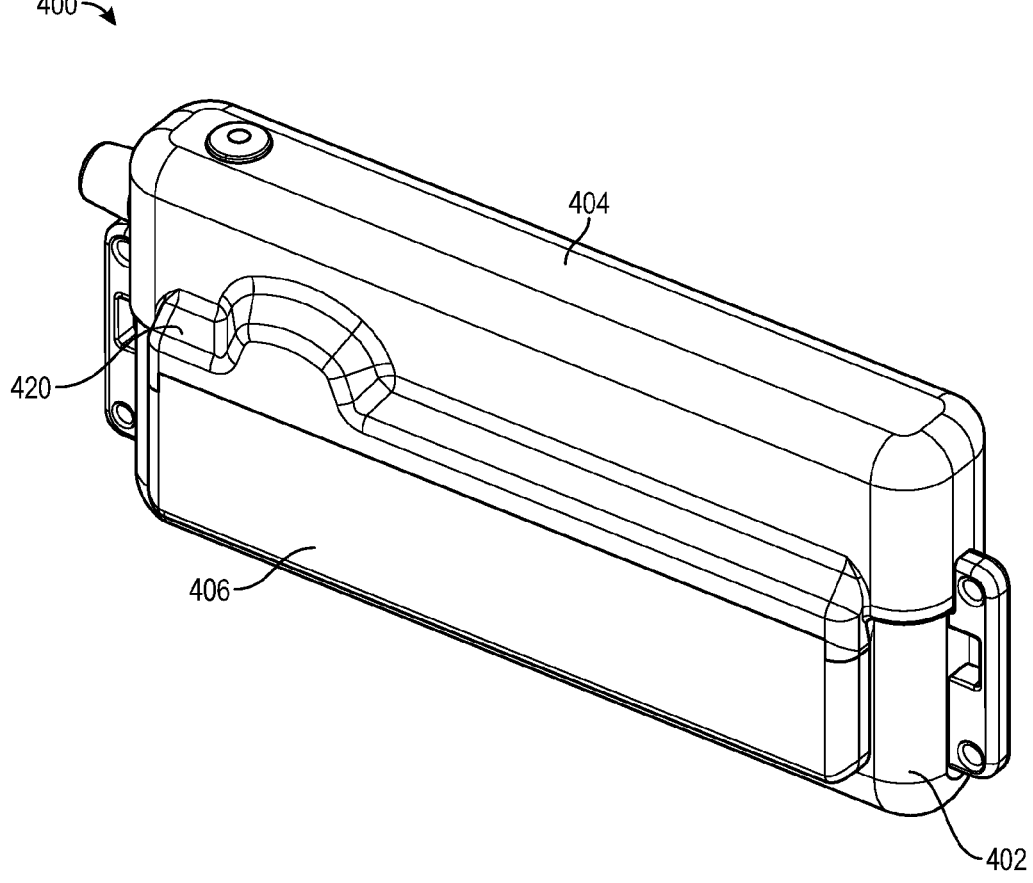
FIG. 4 illustrates a perspective view of an implantable medical device, according to at least one example.
Figure 5:
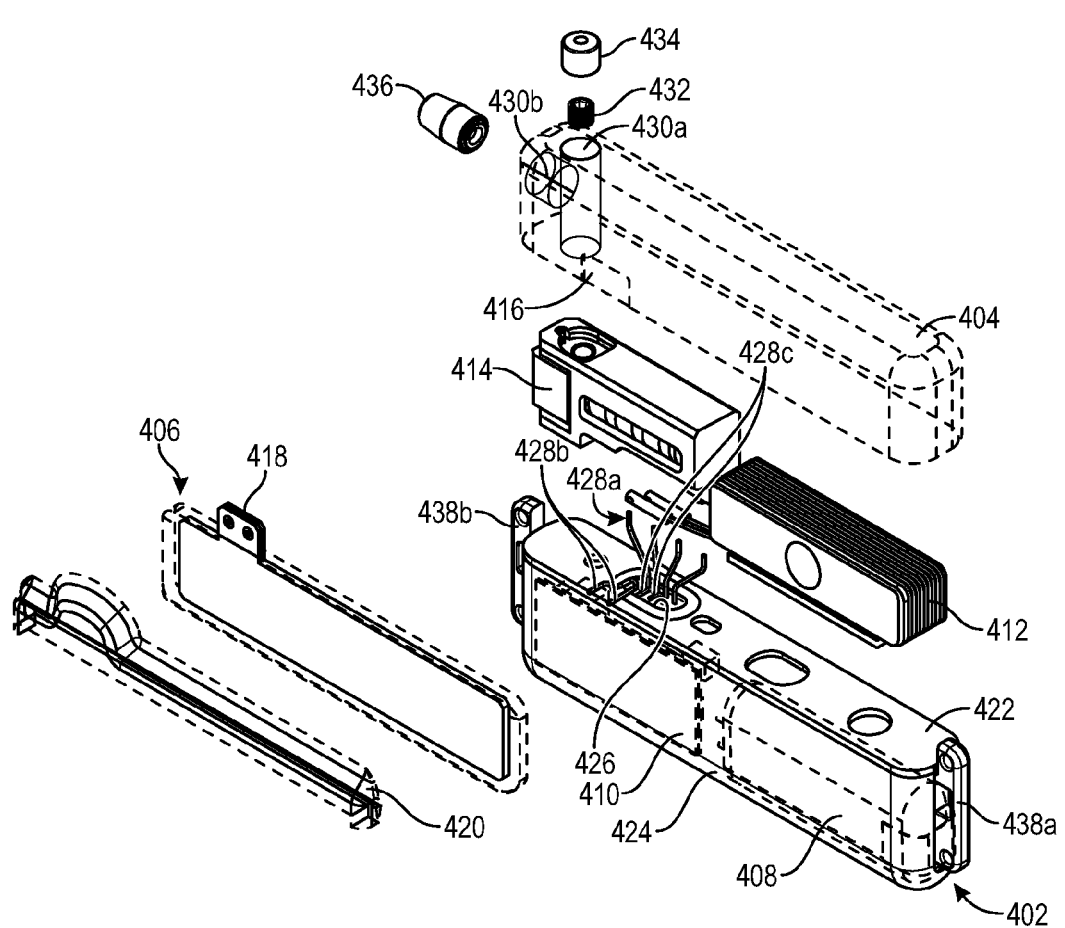
FIG. 5 illustrates an exploded view of the implantable medical device of FIG. 4, according to at least one example.

Referring now to the figures, FIG. 4 and FIG. 5 respectively illustrate a perspective view of an assembled example implantable medical device 400 and an exploded view of the example implantable medical device 400, according to at least one example. The illustrated implantable medical device 400 is an implantable pulse generator ("IPG") medical device for providing neuromodulation therapies. To provide such therapies, the implantable medical device 400 is inserted into a patient's tissue and connected to a neural interface (not shown). The neural interface is placed at a target location within the patient's body. The implantable medical device 400 then delivers electrical signals to the target location using the neural interface and records responses collected by the neural interface. Because the implantable medical device 400 will be inserted or otherwise implanted in the patient's skin, the implantable medical device 400 has a small form factor (e.g., about 40 mm long, about 20 mm tall, and about 7 mm wide in this example) and smooth edges to reduce the potential for patient irritation or injury during and after insertion. In some examples, the dimension of the implantable medical device 400 are greater than those listed or smaller than those listed.

Figure 7A:
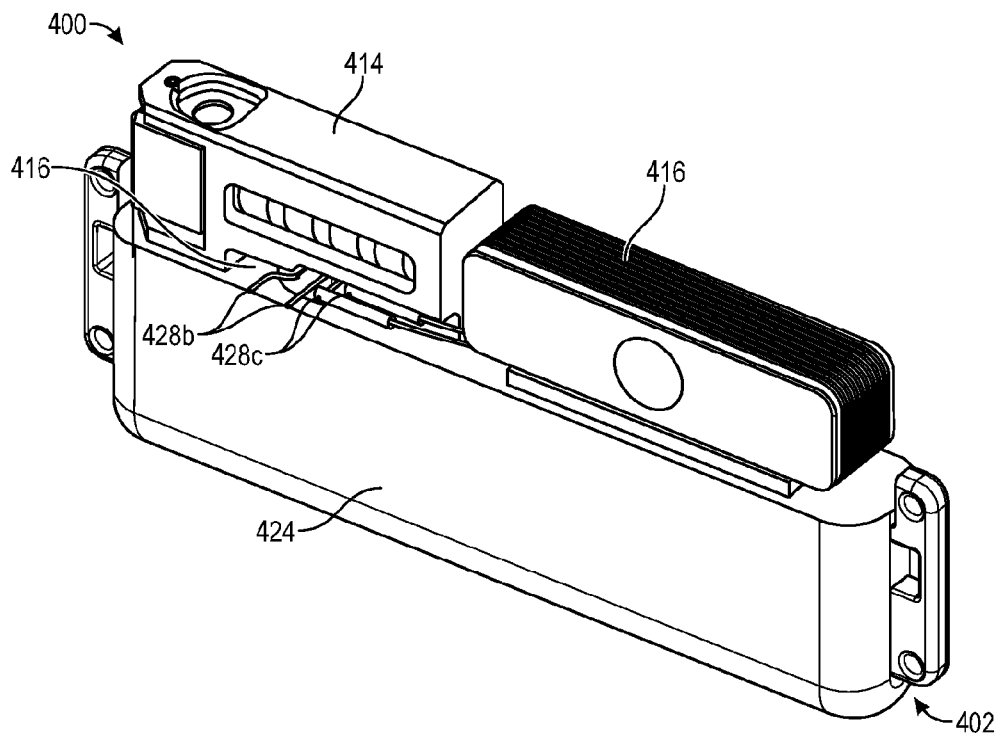
FIG. 7A illustrates a perspective view of a first state of formation of an implantable medical device, according to at least one example.

As illustrated in FIG. 4, generally, the implantable medical device 400 includes an enclosure 402 sometimes referred to as a canister, a header 404, and a communications antenna 406. The enclosure 402 is configured to house active components of the implantable medical device 400 such as one or more power sources 408 (e.g., batteries) and an electronics assembly 410. The enclosure 402 is hermetically sealed thereby keeping the active components free from moisture exposure. The header 404 is configured to encase other active and/or passive components such as a charging antenna 412 and a connector stack 414 that are mounted to the enclosure 402. For example, as illustrated in FIG. 7A, the charging antenna 412 and the connector stack 414 are shown mounted to a lid of the enclosure 402.

Figure 7B:
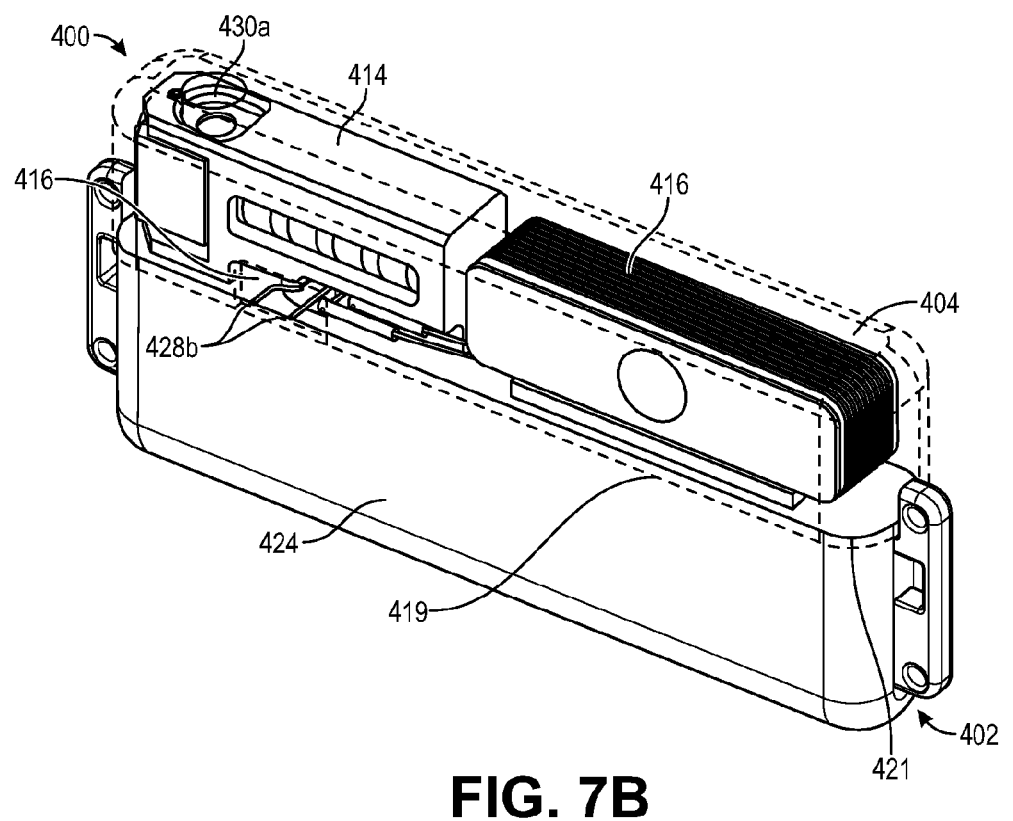
FIG. 7B illustrates a perspective view of a second state of formation of the implantable medical device of FIG. 7A, according to at least one example.

Connection points between the header 404 and the enclosure 402 are also hermetically sealed thereby preventing moisture ingress into the header space of the implantable medical device 400. For example, as illustrated in FIG. 7B, the header 404 can be formed from an epoxy that is over-molded and extends below a top surface of the enclosure 402 such that the header 404 surrounds the top surface of the enclosure 402 and at least a portion of the side walls of the enclosure 402. In FIG. 7B, a perimeter edge 419 of the header 404 extends below a perimeter edge 421 of the enclosure 402. As shown in more detail in FIG. 8, an access window 416 sometimes referred to as a weld window, which is sized and shaped to correspond to a tab 418 of the communications antenna 406, is also defined in the header 404. The access window 416 defines a cutaway region of the header 404 to provide access to components within the header 404.

Figures 7C, 7D:
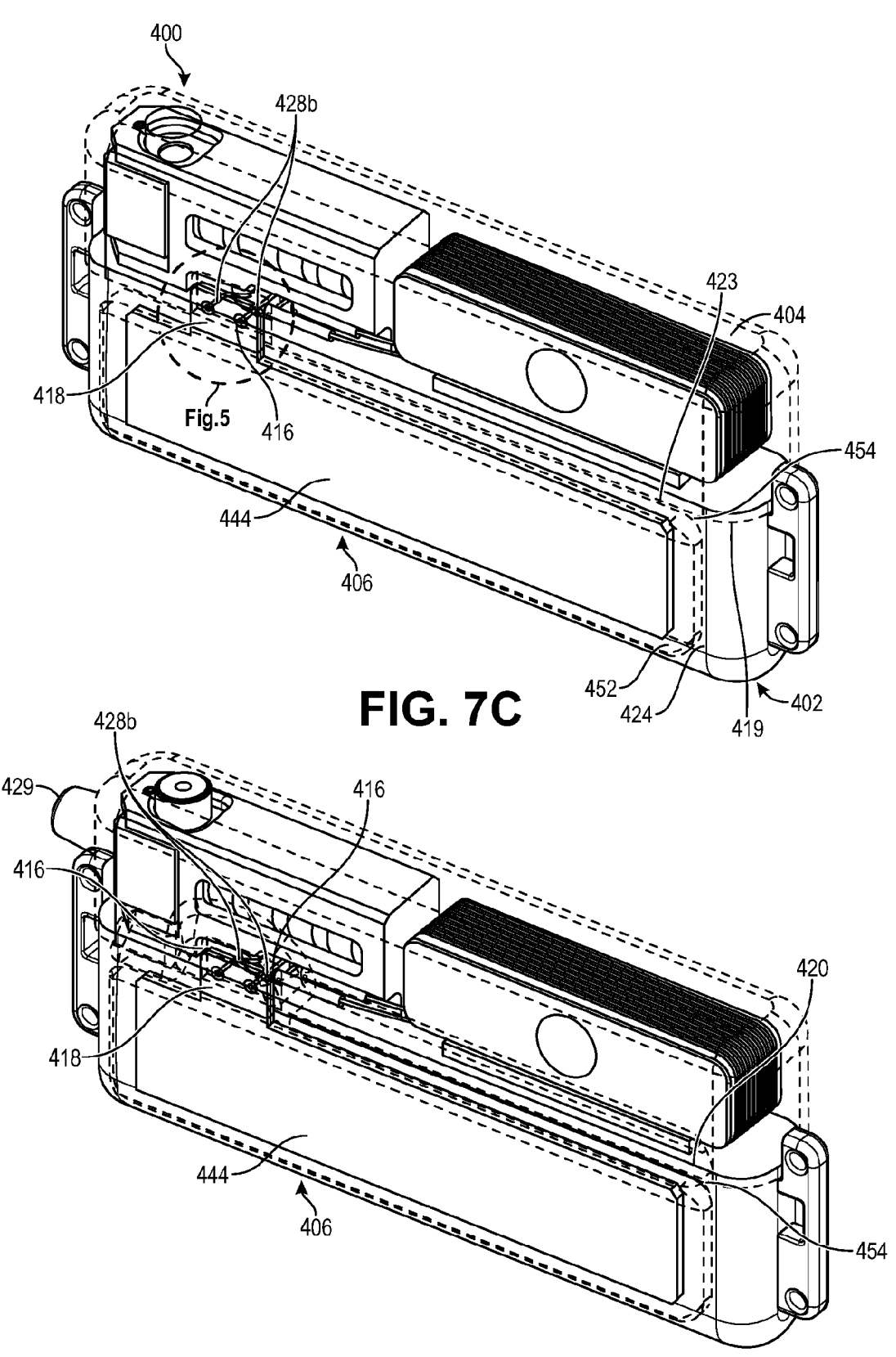
FIG. 7C illustrates a perspective view of a third state of formation of the implantable medical device of FIG. 7A, according to at least one example.
FIG. 7D illustrates a perspective view of a fourth state of formation of the implantable medical device of FIG. 7A, according to at least one example.

The communications antenna 406, which is made as part of a separate process, is connected to the enclosure 402 such that the tab 418 fits within the access window 416, as illustrated in FIG. 7C. This enables electrical connections to be made between components of the implantable medical device 400 with the communications antenna 406. As illustrated in FIG. 7D, once these connections have been made, a backfill 420 is applied to the access window 416 and, in some examples, to an air gap 454 between the communications antenna 406 and the header 404.

Turning now to the enclosure 402, the enclosure 402 includes a lid 422 and a container 424 having at least one side. The enclosure 402 is made from a metallic material such as Titanium or other bio-compatible metallic material. In some examples, some or a portion of the enclosure 402 is made from a different rigid material which may or may not be metallic such as a bio-compatible epoxy. As used herein, the term bio-compatible material refers to a quality of not having toxic or injurious effects on biological systems (especially those of humans) and the capability of the material to exist in harmony with tissue without causing deleterious changes.

The container 424 and the lid 422 together define an interior volume of the enclosure 402. The power source 408 (e.g., battery) and the electronics assembly 410 are mounted inside the interior volume, e.g., to an interior surface of the container 424. The container 424 may be made from a single piece of material or from more than one piece of material. Depending on the shape of the container 424, the container 424 may include more than one side, e.g., a front side to which the communications antenna 406 is mounted, a back side opposite the front side, two lateral sides, and a bottom opposite the lid 422.

The electronics assembly 410 includes one or more electronic components configured for signal processing. For example, the electronics assembly 410 may include a system on chip ("SOC") or system in package ("SIP") that includes any suitable combination components for digital signal processing, analog signal processing, mixed-signal processing, and/or the like that may be present on the surface of a PCB assembly or embedded. Such components may include, for example, a microcontroller, a memory, a timing source, one or more digital interfaces, one or more analog interfaces, voltage regulators, and/or any other suitable component. The electronics assembly 410 may be configured to receive electrical signals from the neural interface, process such signals, and provide additional signals to the neural interface.

In some examples, the electronics assembly 410 includes a processing device and a computer-readable medium, such as a random access memory ("RAM") coupled to the processing device. The processing device may execute computer-executable program instructions stored in memory, such as executing one or more computer programs. Such processing devices may comprise a microprocessor, a digital signal processor ("DSP"), an application-specific integrated circuit ("ASIC"), field programmable gate arrays ("FPGAs"), state machines, or other processing means for processing electrical signals received from neural interface. Such processing means may further include programmable electronic devices such as PLCs, programmable interrupt controllers ("PICs"), programmable logic devices ("PLDs"), programmable read-only memories ("PROMs"), electronically programmable read-only memories ("EPROMs" or "EEPROMs"), or other similar devices.

The processing device may include, or may be in communication with, media, for example computer-readable storage media, that may store instructions that, when executed by the processing device, cause the processing device to perform steps as carried out, or assisted, by a processing device. Examples of computer-readable media may include, but are not limited to a memory chip, ROM, RAM, ASIC, or any other storage means from which a processing device can read or write information.

The container 424 includes smooth edges to minimize irritation during and after implantation. For example, as illustrated, the container 424 has an elongate, rectangular shape with a rounded bottom, i.e., the side opposite the lid 422. The vertical edges of the container 424 are also rounded. In some examples, the container 424 has a different shape than the one illustrated (e.g., round, ovate, square, etc.).

The container 424 includes one or more tabs 438. The tabs 438 may be used for manipulating the container 424 during manufacturing, implantation, or at other times. In some examples, the tabs 438 may be removable. For example, the tabs 438 may include frangible joints such that they can be removed prior to implantation. In some examples, the container 424 does not include the tabs 438.

Once the internal components have been mounted in the container 424, the lid 422 is sealed to the side(s) of the container 424. For example, a perimeter edge of an opening of the container 424 can be welded to a perimeter edge of the lid 422. In this example, the lid 422 is made from a metallic material that is similar to the material of the container 424. The lid 422 may include a small hole, which may be used to backfill the internal volume of the container 424 with helium or other inert gas to provide an inert atmosphere within the internal volume. After which, the small hole may be welded shut. The container 424 and the lid 422, when connected, form a hermetic enclosure.

The lid 422 also includes a feedthrough 426. The feedthrough 426 is an opening that extends through the lid 422 and into the interior volume. The feedthrough 426 is used to pass through a set of feedthrough pins 428. The feedthrough pins 428 are conductive terminals that are connected to one or more of the power source 408, the electronics assembly 410, or other components within the container 424. In some examples, the feedthrough pins 428 carry electrical signals in the form of data and/or power. A first portion 428a of the feedthrough pins 428 are for electrically connecting the connector stack 414, for stimulation and sensing purposes through the neural interface. A second portion 428b of the feedthrough pins 428 are for electrically connecting the communications antenna 406. And a third portion 428c of the feedthrough pins are for electrically connecting the charging antenna 412. While a single feedthrough 426 is illustrated, in some examples, more than one feedthrough 426 is used, any of which may extend through the lid 422 and/or a side wall of the container 424. For example, the first portion 428a and the third portion 428c of the feedthrough pins 428 may extend through the lid 422 and the second portion 428b of the feedthrough pins 428 may extend through the front side wall of the container 424.

Turning now to the connector stack 414 and the charging antenna 412, the connector stack 414 is configured to receive a neural interface. For example, the connector stack 414 may include a port 429 to receive a plug of the neural interface. The connector stack 414 is fixedly mounted to the lid 422 and electrically connected to the first portion 428a of the feedthrough pins 428. The neural interface may include a plurality of conductive leads that are joined together in the plug. The plug, once inserted in to the port 429, connects individual conductive leads to the electronics assembly 410 via the first portion 428a of feedthrough pins. A long axis of the connector stack 414 is aligned with a long axis of the enclosure 402 in this example, though other alignments may be employed in some examples.

The charging antenna 412 is configured to receive an electromagnetic field (e.g., from an external charger) that is converted and used to charge the power source 408 (e.g., battery). The charging antenna 412 takes the form of a coil wrapped around a mandrel, however, the charging antenna 412 may take different form factors. In some examples, the charging antenna 412 receives signals at a different frequency than the communications antenna 406. The charging antenna 412 is fixedly mounted to the lid 422 and electrically connected to the third portion 428c of the feedthrough pins 428. A long axis of the charging antenna 412 is aligned with a long axis of the enclosure 402 in this example, though other alignments may be employed in some examples.

Turning now to the header 404, as illustrated in further detail in FIG. 7B, the header 404 is made from a bio-compatible material such as an epoxy. The header 404 is either made in place or pre-formed and mounted to the lid 422. The header 404 is configured to encapsulate the connector stack 414 and the charging antenna 412. As introduced previously, the header 404 includes the access window 416. The access window 416 is sized and shaped to correspond to the size and shape of the tab 418. Thus, the access window 416 functions as a block-out to enable access to the tab 418. As illustrated in FIG. 7B, the access window 416 also enables access to the second portion 428b of the feedthrough pins 428, e.g., the ones that bent about 90 degrees and extend toward an exterior side surface of the header 404.

The header 404 also includes one or more openings 430. The opening 430a is configured to receive a set screw 432 and a septum 434. The opening 430b is configured to receive a strain relief device 436. In some examples, the plug of the neural interface is inserted into the connector stack 414 via the opening 430b and the strain relief device 436.

Figure 6:
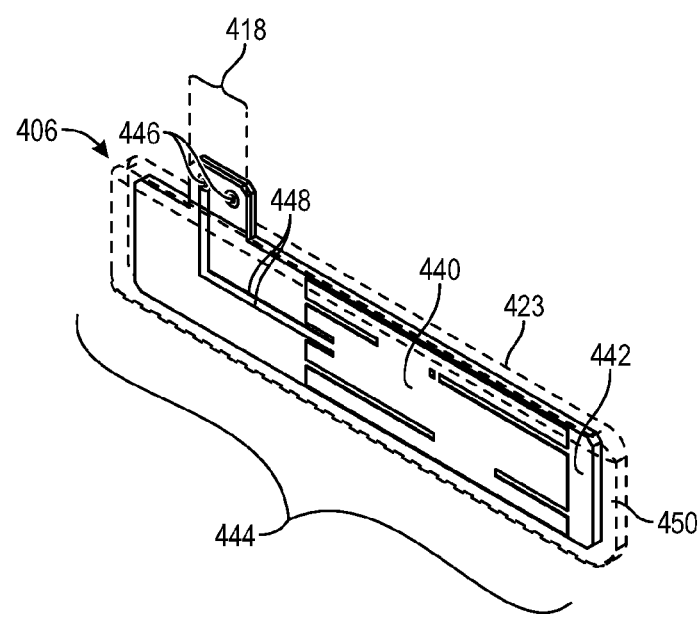
FIG. 6 illustrates a perspective view of a communications antenna, according to at least one example.

As illustrated in greater detail in FIG. 6, the communications antenna 406, which operates according to the Bluetooth® standard, includes a radiating surface 440 attached to a substrate 442 and a ground plane (not shown) located on the opposite, i.e., the side that faces the container 424. In some examples, the communications antenna 406 operates according to different standards or is configured differently. The communications antenna 406 functions to send and receive information relating to operation of the implantable medical device 400, e.g., measured parameters, configuration data, state data, control signals, any other information relating to the implantable medical device 400, etc. The communications antenna 406 may enable pairing/communicating with a second device such as a programming unit, a charger, a mobile phone, or other device located outside the body. In some examples, the communications antenna 406 enables pairing/communicating with other devices located within the body.

The substrate 442, which is ceramic, includes the tab 418 and a main body 444. Thus the tab 418 and the main body 444 are made from the same material and as part of the same substrate 442. The radiating surface 440 is attached to the substrate 442 in any suitable manner. For example, the radiating surface 440 can be deposited, printed, or otherwise attached to the substrate (e.g., pre-formed and glued). The shape of the radiating surface 440 is alterable depending on the radio-frequency characteristics desired. In some examples, the radiating surface 440 has a planar top surface and takes the form of a rectangular metallic plate. In other examples, the radiating surface 440 may take the form of other shapes. The two ferrules are used to connect to each of these circuits that are electrically isolated from each other on the antenna level (there is some coupling on the PCBA side).

The communications antenna 406 also includes a set of conductive terminals 446 located in the tab 418. A first conductive terminal 446 is electrically connected to the radiating surface 440 via a set of conductive traces 448. A second conductive terminal 446 is electrically connected to the ground plane via a second set of conductive traces (not shown). After the radiating surface 440, the conductive terminals 446, and the conductive traces 448 have been made, the main body 444 is fully or partially encapsulated in a bio-compatible and radio frequency (RF)-compatible material such as epoxy or other suitable material. i.e., encapsulation 450. As used herein, the term RF-compatible material refers to a quality of the material that allows RF signals to pass through. In some examples, the RF-compatible material is an RF transparent material or one which RF fields can penetrate with no heat occurring.

In some examples, the entirety of the main body 444 (e.g., all surfaces) may be encapsulated in the encapsulation 450, all surfaces except for the backside surface opposite the container 424 may encapsulated (e.g., a bare backside encapsulation), all surfaces except for a portion of the backside surface opposite the container 424 may be encapsulated (e.g., a partially bare backside encapsulation), or any other suitable combination of surfaces or portions of surfaces may be encapsulated. The main body 444 is horizontally and vertically centered within the encapsulation 450. The depth of the encapsulation 450 on the front side of the communications antenna 406 may be about 0.8 mm and the depth on the back side may be about 0.3 mm. In some examples, the depths are greater than 0.8 mm or less than 0.3 mm. These depths may be selected to tune certain parameters of the communications antenna 406. For example, the operation of the radiating surface 440 may depend on the depth of the encapsulation 450 and/or properties of the epoxy used for the encapsulation 450. In some examples, the epoxy used for the encapsulation 450, the header 404, and other parts of the implantable medical device 400 is EPO-TEK brand MED-301 epoxy. In other examples, other epoxies having different properties are used such as those that are medical grade.

Figure 9:
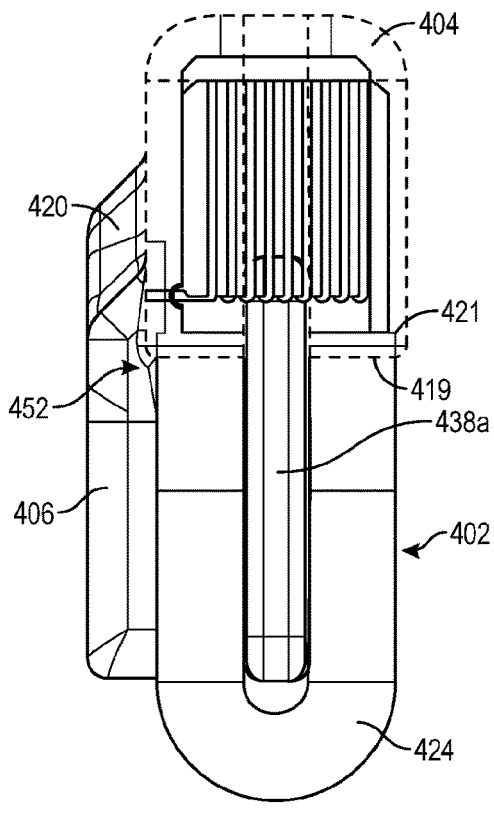
FIG. 9 illustrates an end view of the implantable medical device of FIG. 4, according to at least one example.

As illustrated in FIG. 7C, the communications antenna 406 is connected to an exterior surface of the container 424 (e.g., a mounting location) using any suitable adhesive. For example, additional epoxy, glue, or other adhesive may be applied to a backside of the communications antenna 406 and/or the exterior surface of the container 424 and the two parts may be joined together. The communications antenna 406 is positioned on the exterior surface of the container 424 in a manner that aligns the tab 418 with the access window 416 and forms a narrow air gap 454 between the perimeter edge 419 of the header 404 and a perimeter edge 423 of the communications antenna 406. The air gap 454 may provide volume for the backfill 420 to fill into during subsequent processing steps such as the one illustrated in FIG. 4D. As illustrated in FIG. 9, the air gap 454 is filled in when the backfill 420 is applied.

Figure 8:
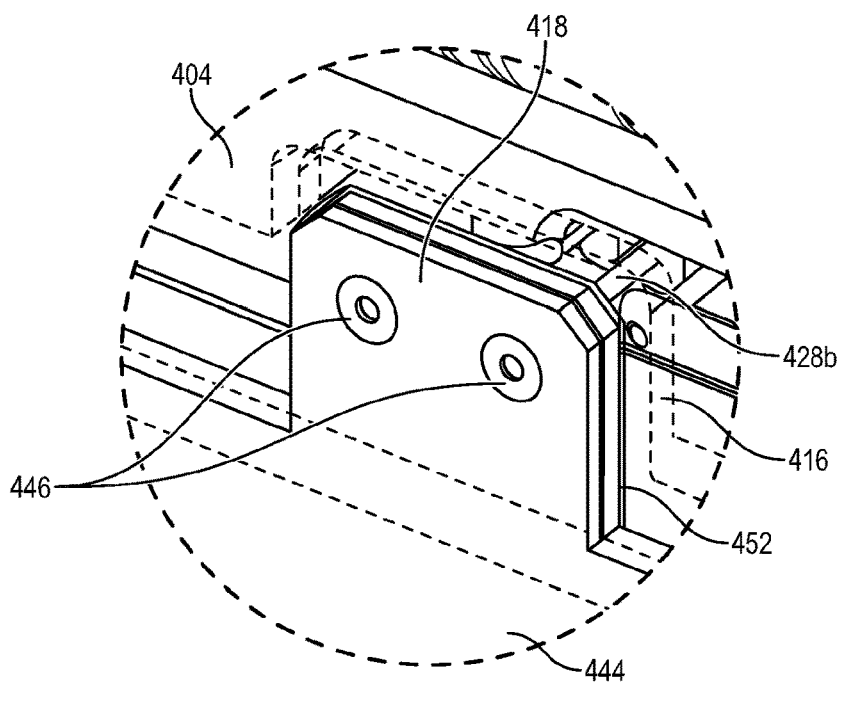
FIG. 8 illustrates a zoomed-in view of a portion of the implantable device illustrated in FIG. 7D, according to at least one example.

As illustrated in FIG. 8, after connecting the communications antenna 406 to the container 424 of the enclosure 402, the set of conductive terminals 446 are electrically connected to the second portion 428b of the set of feedthrough pins 428. In some examples, the set of conductive terminals 446 are plated vias sized and configured to receive the feedthrough pins 428. In some examples, the conductive terminals 446 include ferrules that receive the feedthrough pins 428. The electrical connections between the feedthrough pins 428 and the conductive terminals 446 are achieved using laser welding. In some examples, the electrical connections are made using crimping, soldering, or any other suitable mechanical and/or energetic method.

Turning now to the backfill 420, the backfill 420, although illustrated in FIG. 5 as a rigid component, is a liquid bio-compatible material that, when applied to the implantable medical device 400 has roughly the shape shown in FIG. 5. The purpose of the backfill 420 is to seal up the volume of the access window 416 and, by doing, insulate the electrical connections made in the tab 418 from outside moisture. Another purpose of the backfill 420 is to provide a smooth transition between the perimeter edge 419 of the header 404 and the perimeter edge 423 of the communications antenna 406. In this manner, the backfill 420 may create a filleted transition between the two parts. This distributes stresses across a broader area and makes for a smooth transition between the two parts. In some examples, the backfill 420 extends around additional portions of the perimeter edge of the communications antenna 406, e.g., vertical perimeter edges and horizontal perimeter edge. The backfill 420 can be made from silicone, epoxy, a silicone epoxy mix, other flowable liquid adhesive, and/or any suitable combination of more than one material.

Figure 10:
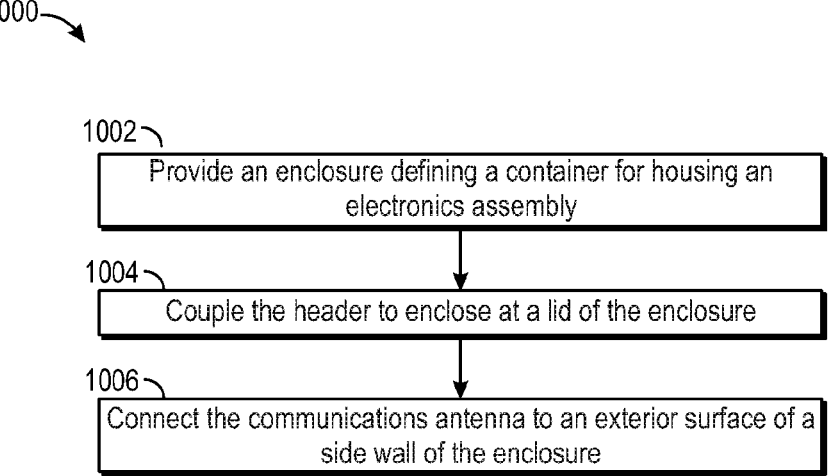
FIG. 10 illustrates a flow chart showing a process for making an implantable medical device, according to at least one example.

FIG. 10 illustrates a flow chart showing a process 1000 for making an implantable medical device such as the implantable medical device 400, according to at least one example. The process 1000 begins at block 1002 by providing an enclosure 402 defining a container 424 for housing an electronics assembly 410. The process 1000 may also include mounting at least one of a power source 408 and/or the electronics assembly 410 in the container 424.

At block 1004, the process 1000 includes coupling a header 404 to enclose at least a top portion of the enclosure 402. In some examples, this may include attaching a pre-manufactured header 404 in place or making the header 404 in place. The header 404 includes an access window 416 located at the perimeter edge 419 of the header 404. At least some portion of set of conductive leads extend through the access window 416. For example, as illustrated in FIG. 4A, the first portion 428a of feedthrough pins, after coming through the feedthrough 426, include about a 90 degree bend to put distal ends of the first portion 428a of feedthrough pins in a position where they can be mated with the conductive terminals 446 of a tab 418 of a communications antenna 406.

At block 1006, the process 1000 includes connecting the communications antenna 406 to an exterior surface of a side wall of the enclosure 402. In this example, the communications antenna 406 includes a main body 444 and an electrical termination tab (e.g., the tab 418) that indexes in the access window 416 and aligns the set of conductive terminals 446 disposed in the electrical termination tab 418 with the set of conductive leads. In some examples, the electrical termination tab extends beyond the perimeter edge 421 of the enclosure 402 (e.g., beyond the lid 422) when the communications antenna 406 is connected to the enclosure 402.

In some examples, the main body 444 of the communications antenna 406 is encased in a bio-compatible material such as an encapsulation 450. In some examples, the header 404 is made from a different bio-compatible material such as a different epoxy having different properties. Different epoxies may be selected to provide different radio-frequency (RF) properties, some for the communications antenna 406 and some for the charging antenna 412.

In some examples, the block 1006 includes applying an adhesive to at least one of the communications antenna 406 or the side wall (e.g., a wall of the container 424), and mating together the communications antenna 406 and the side wall, with the adhesive disposed between the communications antenna 406 and the side wall.

In some examples, the process 1000 further includes electrically connecting the set of conductive terminals 446 with the set of conductive leads. In some examples, this includes using laser welding.

In some examples, the process 1000 further includes, after connecting the communications antenna 406 at the block 1006, placing a backfill 420 in the access window 416 to at least cover the set of conductive terminals 446. In this example, the block 708 includes placing the communications antenna 406 in a manner that an air gap 454 is formed between the perimeter edge 419 of the header 404 and a perimeter edge 423 of the communications antenna 406. In this example, the backfill 420 is also placed in the air gap 454 to create a transition between the header 404 and the communications antenna 406.

In some examples, the process 1000 further includes prior to performing the block 1006, making the communications antenna 406. This may include making the main body 444 and the electrical termination tab 418 in a ceramic substrate 442, making a metallic plate as the radiating surface 440 in the main body 444 of the ceramic substrate 442, making the pair of conduct terminals 446 in the electrical termination tab 418, making a pair of conductive traces 448 in the ceramic substrate 442 that electrically connect the metallic plate of the radiating surface 440 and at least one of pair of conductive terminals 446, and encasing the main body 444 in a bio-compatible material (e.g., the encapsulation 450) without encasing the electrical termination tab 418.

In some examples, the process 1000 further includes making a set of conductive leads (e.g., the feedthrough pins 428) that extend from the electronics assembly 410 and through the enclosure 402. In some examples, the set of conductive leads extend through a feedthrough 426 disposed in the lid 422 of the enclosure 402.

In the following, further examples are described to facilitate the understanding of the present disclosure.

Example 1. In this example, there is provided an implantable device, including:

an enclosure including a lid and a side wall connected to the lid;

an electronics assembly disposed within an interior volume of the enclosure;

a set of conductive leads electrically connected to the electronics assembly and extending through the enclosure; and a communications antenna disposed on an exterior surface of the side wall and including a main body and a tab, the tab including a set of conductive terminals, wherein the main body is coated in a bio-compatible material and the set of conductive terminals is electrically connected to the set of conductive leads.

Example 2. In this example, there is provided a device of any of the preceding or subsequent examples, further including a header connected to the lid of the enclosure, and wherein the main body of the communications antenna is not disposed within the header.

Example 3. In this example, there is provided a device of any of the preceding or subsequent examples, further including:

a charging antenna connected to the lid; and a connector stack connected to the lid, wherein a second set of conductive leads extends through the enclosure and electrically connects the electronics assembly to at least one of the connector stack or the charging antenna.

Example 4. In this example, there is provided a device of any of the preceding or subsequent examples, further including an epoxy header that encloses the charging antenna and the connector stack.

Example 5. In this example, there is provided a device of any of the preceding or subsequent examples, wherein each conductive lead of the set of conductive leads extends through the lid of the enclosure in a first direction and includes a bend that orients a distal tip of the respective conductive lead in a second direction.

Example 6. In this example, there is provided a device of any of the preceding or subsequent examples, wherein the enclosure hermetically seals the interior volume.

Example 7. In this example, there is provided a device of any of the preceding or subsequent examples, wherein the bio-compatible material is RF-compatible.

Example 8. In this example, there is provided a device of any of the preceding or subsequent examples, wherein the communications antenna further comprises a metallic plate made on a ceramic substrate, and the set of conductive terminals is electrically connected to the metallic plate via a set of conductive traces.

Example 9. In this example, there is provided a device of any of the preceding or subsequent examples, wherein the main body and the tab are made from the ceramic substrate, with the metallic plate disposed in the main body.

Example 10. In this example, them is provided a device of any of the preceding or subsequent examples, wherein the communications antenna further includes a first metallic plate made on a first side of a ceramic substrate and a second metallic plate made on a second side of the ceramic substrate, and the set of conductive terminals is electrically connected to at least one of the first or second metallic plates via a set of conductive traces.

Example 11. In this example, there is provided a device of any of the preceding or subsequent examples, wherein the main body and the tab are made from the ceramic substrate, with the metallic plate disposed in the main body.

Example 12. In this example, there is provided a method, including providing an enclosure including an electronics assembly;

coupling a header to enclose at least a lid of the enclosure, wherein an access window is formed at a perimeter edge of the header, a set of conductive leads extending from the electronics assembly and through the access window; and connecting a communications antenna to an exterior surface of a side wall of the enclosure, the communications antenna including a body and an electrical termination tab that corresponds in size and shape to the access window and aligns a set of conductive terminals disposed in the electrical termination tab with the set of conductive leads.

Example 13. In this example, there is provided a method of any of the preceding or subsequent examples, further including electrically connecting the set of conductive terminals with the set of conductive leads.

Example 14. In this example, there is provided a method of any of the preceding or subsequent examples, wherein the body of the communications antenna is made from a ceramic substrate that is coated in a bio-compatible material.

Example 15. In this example, there is provided a method of any of the preceding or subsequent examples, wherein the header is made from a second bio-compatible material.

Example 16. In this example, there is provided a method of any of the preceding or subsequent examples, wherein the electrical termination tab extends beyond a perimeter edge of the lid of the enclosure.

Example 17. In this example, there is provided a method of any of the preceding or subsequent examples, wherein electrically connecting the set of conductive terminals with the set of conductive leads includes at least one of soldering, crimping, or laser welding.

Example 18. In this example, there is provided a method of any of the preceding or subsequent examples, wherein connecting the communications antenna to the exterior surface of the side wall includes:

applying an adhesive to at least one of the communications antenna or the side wall, and mating together the communications antenna and the side wall, with the adhesive disposed between the communications antenna and the side wall.

Example 19. In this example, there is provided a method of any of the preceding or subsequent examples, further including making the header.

Example 20. In this example, there is provided a method of any of the preceding or subsequent examples, wherein making the header includes:

making the header as a separate part, and fitting the header in place on the lid of the enclosure after making the header.

Example 21. In this example, there is provided a method of any of the preceding or subsequent examples, further including, after connecting the communications antenna, placing a backfill material in the access window to cover at least the set of conductive terminals.

Example 22. In this example, there is provided a method of any of the preceding or subsequent examples, wherein connecting the communications antenna to the exterior surface of the side wall includes connecting the communications antenna at a particular mounting location on the exterior surface that defines an air gap between the header and the communications antenna, and wherein placing the backfill material further includes placing the backfill material in the air gap.

Example 23. In this example, there is provided a method of any of the preceding or subsequent examples, further including, prior to connecting the communications antenna, making the communications antenna by at least:

making the body and the electrical termination tab in a ceramic substrate;

making a metallic plate in the body of the ceramic substrate;

making the set of conduct terminals in the electrical termination tab;

making a pair of electrical traces in the ceramic substrate that electrically connecting the metallic plate and the set of conductive terminals; and encasing the body in a bio-compatible material without encasing the electrical termination tab.

Example 24. In this example, there is provided a method of any of the preceding or subsequent examples, further including, prior to connecting the communications antenna, making the communications antenna by at least:

making the body and the electrical termination tab in a ceramic substrate;

making a first metallic plate in a first side of the body of the ceramic substrate;

making a second metallic plate in a second side of the body of the ceramic substrate;

making the set of conductive terminals in the electrical termination tab;

making a set of electrical traces in the ceramic substrate that electrically connect the first and second metallic plates and the set of conductive terminals; and encasing the body in a bio-compatible material without encasing the electrical termination tab.

Example 25. In this example, there is provided a system, including:

an implantable medical device, including:

an enclosure to house an electronics assembly, the enclosure including a lid and a side connected to the lid; and a set of conductive leads to extend from the electronics assembly to outside the enclosure via the lid; and an antenna that connects to an exterior surface of the side at a mounting location, the antenna including a body portion encased in a bio-compatible material;

a tab portion connected to the body portion; and a set of conductive terminals disposed in the tab portion and that align with the set of conductive leads when the antenna is connected to the exterior surface at the mounting location.

Example 26. In this example, there is provided a system of any of the preceding or subsequent examples, wherein the antenna further includes a metallic plate disposed in the body portion and a set of conductive traces extending between the metallic plate and the set of conductive leads.

Example 27. In this example, there is provided a system of any of the preceding or subsequent examples, wherein a distal end of the tab portion extends beyond the lid of the enclosure when the antenna is connected to the exterior surface at the mounting location.

Example 28. In this example, there is provided a system of any of the preceding or subsequent examples, wherein the antenna includes an elongate shape.

Example 29. In this example, there is provided a system of any of the preceding or subsequent examples, wherein the implantable medical device further includes a header to encase at least the lid of the enclosure, wherein an access window is formed in the header that corresponds in shape to the tab portion.

Example 30. In this example, there is provided a system of any of the preceding or subsequent examples, wherein the bio-compatible material is epoxy and the header is made from the epoxy.

Example 31. In this example, there is provided a system of any of the preceding or subsequent examples, further including a backfill to fill in the access window and to extend along at least a portion of the body portion adjacent the access window.

Example 32. In this example, there is provided a system of any of the preceding or subsequent examples, wherein the antenna operates in accordance with the Bluetooth® standard.

Example 33. In this example, there is provided a device, including:

an enclosure including a lid and a side wall;

an electronics assembly disposed within an interior volume of the enclosure and including a plurality of conductive leads that extend through the lid of the enclosure;

one or more electrical components connected to an exterior surface of the lid and electrically connected to a first portion of the plurality of conductive leads; and a header that encapsulates the one or more electrical components and includes an access window through which extends a second portion of the plurality of conductive leads, the access window sized to receive a tab of a communications antenna.

Example 34. In this example, them is provided a device of any of the preceding or subsequent examples, further including the communications antenna, the communications antenna including the tab and a body.

Example 35. In this example, there is provided a device of any of the preceding or subsequent examples, wherein the body of the communications antenna is connected to an exterior surface of the side wall such that the tab aligns with the access window.

Example 36. In this example, there is provided a device of any of the preceding or subsequent examples, wherein the tab includes a set of conductive terminals that is electrically connected to the second portion of conductive leads.

Example 37. In this example, there is provided a device, including:

an enclosure for housing an electronics assembly, the enclosure including a lid and a side wall connected to the lid;

a set of conductive pins extending through the lid of the enclosure; and a communications antenna connected to an exterior surface of the side wall, the communications antenna including a set of conductive terminals, wherein the set of conductive pins is received by and electrically connected to the set of conductive terminals.

Example 38. In this example, there is provided a device of any of the preceding or subsequent examples, further including:

one or more electrical components connected to the lid; and a header connected to the lid and encasing the lid and the one or more electrical components.

Example 39. In this example, there is provided a device of any of the preceding or subsequent examples, further wherein the header physically contacts the side wall.

Example 40. In this example, there is provided a device of any of the preceding or subsequent examples, further including a silicone backfill that physically contacts the header and at least a portion of the communications antenna.

Example 41. In this example, there is provided a device, including:

one or more electrical components connected to the lid;

a header connected to the lid and encasing the lid and the one or more electrical components; and a communications antenna connected to an exterior surface of the side wall at a mounting location that is outside of the header.

Example 42. In this example, there is provided a device of any of the preceding or subsequent examples, further including a set of conductive pins extending through the lid of the enclosure, wherein the set of conductive pins is received by and electrically connected to a set of conductive terminals disposed in a terminal portion of the communications antenna.

Example 43. In this example, there is provided a device of any of the preceding or subsequent examples, further wherein the header physically contacts the side wall.

Example 44. In this example, them is provided a device of any of the preceding or subsequent examples, further including a silicone backfill that physically contacts the header and at least a portion of the communications antenna.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated examples thereof are shown in the drawings and have been described above in detail. It should be understood, however, that there is no intention to limit the disclosure to the specific form or forms disclosed, but on the contrary, the intention is to cover all modifications, alternative constructions and equivalents falling within the spirit and scope of the disclosure, as defined in the appended claims.

The use of the terms "a" and "an" and "the" and similar referents in the context of describing the disclosed examples (especially in the context of the following claims) are to be construed to cover both the singular and the plural, unless otherwise indicated herein or clearly contradicted by context. The terms "comprising," "having," "including," and "containing" are to be construed as open-ended terms (e.g., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate examples of the disclosure and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is otherwise understood within the context as used in general to present that an item, term, etc., may be either X, Y, or Z, or any combination thereof (e.g., X, Y, and/or Z). Thus, such disjunctive language is not generally intended to, and should not, imply that certain examples require at least one of X, at least one of Y, or at least one of Z to each be present. [0153] Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and all three of A and B and C.

Preferred examples of this disclosure are described herein, including the best mode known to the inventors for carrying out the disclosure. Variations of those preferred examples may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

It is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure.

All references, including publications, patent applications, and patents, cited herein are hereby incorporated by reference to the same extent as if each reference were individually and specifically indicated to be incorporated by reference and were set forth in its entirety herein.

While the principles of the disclosure have been described above in connection with specific apparatuses and methods, it is to be clearly understood that this description is made only by way of example and not as limitation on the scope of the disclosure.

What is claimed is:

1. An implantable pulse generator comprising:
a power source;
a wireless communication component configured to facilitate wireless communication with a non-implanted device, wherein the wireless communication component comprises an antenna that comprises a main body comprising one or more patterned planar conductive elements and a tab comprising a set of conductive terminals electrically connected to one or more leads, wherein each of at least one of the one or more patterned planar conductive elements is positioned on an outer surface of the implantable pulse generator and wherein the antenna is adhesively sealed to the outer surface of the implantable pulse generator;
pulse-generating circuitry connected to the power source; and
one or more lead connections, wherein each lead connection of the one or more lead connections is electrically connected to the pulse-generating circuitry to enable the lead to deliver at least part of an electrical output stimuli triggered by the pulse-generating circuitry.

2. The implantable pulse generator of claim 1, further comprising one or more suture engagement components, wherein each suture engagement component of the one or more suture engagement components includes one or more holes each having a diameter that is at least 0.1 mm and less than 5 mm.

3. The implantable pulse generator of claim 2, wherein:
a first suture-engagement component of the one or more suture-engagement components includes a first outer portion of the implantable pulse generator, wherein each of one or more first holes extend through, along a depth dimension, the first outer portion; and
a second suture-engagement component of the one or more suture-engagement components includes a second outer portion of the implantable pulse generator, wherein one or more second holes extend through, along the depth dimension the second outer portion, wherein each of the one or more second holes is separated from at least one of the one or more first holes by a separation distance that is at least 90% of a length of the implantable pulse generator, wherein the length of the implantable pulse generator is perpendicular to and longer than each of a depth of the implantable pulse generator and a width of the implantable pulse generator.

4. The implantable pulse generator of claim 2, wherein the one or more suture-engagement components are configured such the one or more suture-engagement components include:
at least one first hole, wherein each first hole of the at least one first hole:
is positioned such that a center of the first hole is less than 5 mm from a first edge of the implantable pulse generator; and has a diameter that is at least 0.1 mm and less than 5 mm; and at least one second hole, wherein each second hole of the at least one second hole:

is positioned such that a center of the second hole is less than 5 mm from a second edge of the implantable pulse generator, the second edge being opposite from and parallel to the first edge; and has a diameter that is at least 0.1 mm and less than 5 mm.

5. The implantable pulse generator of claim 1, further comprising:

one or more housings, wherein each of the one or more housings at least partly encases:

the power source;

the wireless communication component; and/or the pulse-generating circuitry wherein each of the one or more suture-engagement components is attached to at least one of the one or more housings.

6. The implantable pulse generator of claim 2, wherein each of the one or more suture-engagement components includes a planar surface, and wherein each of the one or more holes extends through the planar surface.

7. The implantable pulse generator of claim 2, wherein each of the one or more suture-engagement components includes a wrapped surface, and wherein each of the one or more holes extends through two opposite portions of the wrapped surface.

8. The implantable pulse generator of claim 2, wherein each of the one or more suture-engagement components includes a metallic material.

9. The implantable pulse generator of claim 2, wherein the one or more suture-engagement components are configured so as to collectively include at least four holes.

10. The implantable pulse generator of claim 2, wherein each suture-engagement component of the one or more suture-engagement components includes one or more holes each having a diameter that is at least 0.5 mm and less than 2.5 mm.

11. The implantable pulse generator of claim 1, further comprising:

a can housing that houses the pulse-generating circuitry, wherein the antenna is positioned such that at least part of the antenna is on a surface of the can housing.

12. The implantable pulse generator of any one of claims 1-11, wherein the power source includes a rechargeable battery.

13. The implantable pulse generator of claim 1, wherein the pulse-generating circuitry is configured to:

identify, based on wireless communication with the non-implanted device, temporal and amplitude characteristics for electrical pulse stimuli; and trigger electrical output stimuli having the temporal and amplitude characteristics.

14. An implantable pulse generator comprising:

a power source;

pulse-generating circuitry connected to the power source;

one or more lead connections, wherein each lead connection of the one or more lead connections is:

electrically connected to the pulse-generating circuitry to enable the lead to deliver at least part of the electrical output stimuli triggered by the pulse-generating circuitry;

a can housing that houses the pulse-generating circuitry; and a wireless communication component configured to facilitate wireless communication with a non-implanted device, wherein the wireless communication component comprises an antenna that is positioned such that at least part of the antenna is on a surface of the can housing, the antenna comprising:

a main body; and a tab, the tab comprising a set of conductive terminals, wherein the set of conductive terminals is electrically connected to one or more leads, and wherein the antenna is adhesively sealed to the outer surface of the implantable pulse generator.

15. The implantable pulse generator of claim 14, wherein the pulse-generating circuitry is configured to:

identify, based on wireless communication with the non-implanted device, temporal and amplitude characteristics for electrical pulse stimuli; and trigger electrical output stimuli having the temporal and amplitude characteristics; and wherein the one or more lead connection is shaped to engage a lead.

* * * * *